United States Patent
Larzon et al.

(10) Patent No.: US 11,179,145 B2
(45) Date of Patent: Nov. 23, 2021

(54) COLLAPSIBLE TUBE FOR HEMOSTASIS

(71) Applicant: M-V ARTERICA AB, Gothenburg (SE)

(72) Inventors: Thomas Larzon, Örebro (SE); Cecilia Larzon, Gothenburg (SE)

(73) Assignee: M-V ARTERICA AB, Gothenburg (SE)

( * ) Notice: Subject to any disclaimer, the term of this patent is extended or adjusted under 35 U.S.C. 154(b) by 154 days.

(21) Appl. No.: 16/190,654

(22) Filed: Nov. 14, 2018

(65) Prior Publication Data
US 2019/0142402 A1 May 16, 2019

Related U.S. Application Data

(60) Provisional application No. 62/587,341, filed on Nov. 16, 2017.

(51) Int. Cl.
*A61B 17/04* (2006.01)
*A61B 17/00* (2006.01)
*A61M 39/06* (2006.01)

(52) U.S. Cl.
CPC ...... *A61B 17/0057* (2013.01); *A61B 17/0401* (2013.01); *A61M 39/0613* (2013.01); *A61B 2017/00592* (2013.01); *A61B 2017/00597* (2013.01); *A61B 2017/00637* (2013.01); *A61B 2017/00663* (2013.01); *A61B 2017/00672* (2013.01); *A61B 2017/00676* (2013.01); *A61B 2017/0409* (2013.01); *A61B 2017/0427* (2013.01); *A61L 2400/04* (2013.01);
(Continued)

(58) Field of Classification Search
CPC ............. A61L 2400/04; A61B 17/0401; A61B 2017/00597; A61B 2017/00663; A61B 2017/00672; A61B 2017/00575; A61B 2017/00659; A61B 2017/0061; A61B 2017/00592; A61B 2017/0057; A61B 2017/042–0425; A61B 2017/0409
See application file for complete search history.

(56) References Cited

U.S. PATENT DOCUMENTS

| 5,108,421 A | 4/1992 | Fowler |
| 5,364,408 A | 11/1994 | Gordon |
| 5,391,183 A | 2/1995 | Janzen et al. |

(Continued)

FOREIGN PATENT DOCUMENTS

| EP | 2095774 | 9/2009 |
| EP | 2308521 | 4/2011 |

(Continued)

OTHER PUBLICATIONS

Final Office Action dated Oct. 3, 2019 in U.S. Appl. No. 15/277,542, filed Sep. 27, 2016 published as 2017-0086804 on Mar. 30, 2017.
(Continued)

*Primary Examiner* — Katherine H Schwiker
(74) *Attorney, Agent, or Firm* — Schmeiser, Olsen & Watts LLP

(57) ABSTRACT

Collapsible tube embodiments may be used to promote hemostasis at surgical sites or any other suitable location. In some cases, vascular closure device embodiments may include collapsible tube embodiments in order to promote hemostasis at a surgical site during a vascular closure procedure.

24 Claims, 15 Drawing Sheets

(52) U.S. Cl.
CPC ............... *A61M 2039/062* (2013.01); *A61M 2039/0673* (2013.01)

(56) References Cited

U.S. PATENT DOCUMENTS

| | | | |
|---|---|---|---|
| 5,413,571 A | 5/1995 | Katsaros et al. | |
| 5,417,699 A | 5/1995 | Klein et al. | |
| 5,507,744 A | 4/1996 | Tay et al. | |
| 5,540,704 A | 7/1996 | Gordon et al. | |
| 5,626,601 A | 5/1997 | Gershony et al. | |
| 5,700,273 A | 12/1997 | Buelna et al. | |
| 5,716,375 A | 2/1998 | Fowler | |
| 5,725,551 A | 3/1998 | Meyers et al. | |
| 5,728,134 A | 3/1998 | Barak | |
| 5,730,725 A | 3/1998 | Yoon | |
| 5,868,762 A | 2/1999 | Cragg et al. | |
| 6,048,358 A | 4/2000 | Barak | |
| 6,059,800 A | 5/2000 | Hart et al. | |
| 6,231,561 B1 | 5/2001 | Frazier et al. | |
| 6,626,918 B1 | 9/2003 | Ginn et al. | |
| 7,789,893 B2 | 9/2010 | Drasler et al. | |
| 8,617,204 B2 | 12/2013 | Khosravi et al. | |
| 8,821,532 B2 | 9/2014 | Schaeffer | |
| 8,920,442 B2 | 12/2014 | Sibbitt, Jr. et al. | |
| 9,687,216 B2 | 6/2017 | Sawhney et al. | |
| 9,782,156 B2 | 10/2017 | Larzon et al. | |
| 2002/0026208 A1 | 2/2002 | Roe et al. | |
| 2002/0045908 A1 | 4/2002 | Nobles et al. | |
| 2002/0077581 A1 | 6/2002 | Davidner et al. | |
| 2005/0149066 A1 | 7/2005 | Stafford | |
| 2005/0251155 A1 | 11/2005 | Orban, III | |
| 2006/0069397 A1 | 3/2006 | Nobles et al. | |
| 2006/0135991 A1* | 6/2006 | Kawaura | A61B 17/0057 606/213 |
| 2006/0142784 A1 | 6/2006 | Kontos | |
| 2007/0083231 A1 | 4/2007 | Lee | |
| 2007/0203506 A1 | 8/2007 | Sibbitt, Jr. et al. | |
| 2007/0276413 A1 | 11/2007 | Nobels | |
| 2008/0097509 A1 | 4/2008 | Beyar et al. | |
| 2008/0147112 A1 | 6/2008 | Sheets et al. | |
| 2008/0177288 A1 | 7/2008 | Carlson | |
| 2008/0300629 A1 | 12/2008 | Surti | |
| 2009/0254119 A1 | 10/2009 | Sibbitt, Jr. et al. | |
| 2009/0264922 A1 | 10/2009 | Mas | |
| 2010/0179590 A1 | 7/2010 | Fortson et al. | |
| 2010/0217308 A1* | 8/2010 | Hansen | A61B 17/0057 606/213 |
| 2010/0217311 A1 | 8/2010 | Jenson et al. | |
| 2010/0217312 A1* | 8/2010 | Hill | A61B 17/0057 606/213 |
| 2010/0262166 A1* | 10/2010 | Boraiah | A61B 17/34 606/148 |
| 2011/0077668 A1 | 3/2011 | Gordon et al. | |
| 2011/0218568 A1* | 9/2011 | Voss | A61B 17/0469 606/232 |
| 2012/0010633 A1 | 1/2012 | Noda et al. | |
| 2012/0158045 A1 | 6/2012 | Pipenhagen | |
| 2012/0290001 A1 | 11/2012 | Uchida et al. | |
| 2012/0296373 A1 | 11/2012 | Roorda et al. | |
| 2013/0006297 A1 | 1/2013 | Drasler | |
| 2013/0190812 A1 | 7/2013 | Vidlund | |
| 2013/0231701 A1 | 9/2013 | Voss et al. | |
| 2014/0039547 A1* | 2/2014 | White | A61B 17/0057 606/213 |
| 2014/0076955 A1 | 3/2014 | Lorenz | |
| 2014/0257359 A1 | 9/2014 | Tegels et al. | |
| 2015/0005810 A1 | 1/2015 | Center et al. | |
| 2015/0066055 A1 | 3/2015 | Sibbitt, Jr. et al. | |
| 2015/0105805 A1 | 4/2015 | Fortson | |
| 2015/0142049 A1 | 5/2015 | Delgado et al. | |
| 2015/0265350 A1 | 9/2015 | Shimizu et al. | |
| 2016/0228109 A1* | 8/2016 | Jacobs | A61B 17/0057 |
| 2016/0242793 A1* | 8/2016 | Norton | A61B 17/0401 |
| 2017/0086804 A1 | 3/2017 | Larzon et al. | |
| 2017/0086807 A1 | 3/2017 | Larzon et al. | |
| 2018/0049731 A1 | 2/2018 | Hardy et al. | |
| 2019/0142403 A1 | 5/2019 | Nyman | |
| 2020/0046343 A1 | 2/2020 | Kramer | |
| 2020/0129164 A1 | 4/2020 | Larzon et al. | |
| 2020/0155817 A1 | 5/2020 | Kassab et al. | |

FOREIGN PATENT DOCUMENTS

| | | |
|---|---|---|
| JP | 2005-511130 | 4/2005 |
| WO | WO 97/03613 | 2/1997 |
| WO | WO 10/081103 | 7/2010 |
| WO | WO 17/019525 | 2/2017 |
| WO | WO 18/195274 | 10/2018 |
| WO | WO 20/081864 | 4/2020 |
| WO | WO 20/085983 | 4/2020 |
| WO | WO 21/102044 | 5/2021 |

OTHER PUBLICATIONS

Notice of Allowance dated Jan. 2, 2020 in U.S. Appl. No. 15/277,542, filed Sep. 27, 2016 published as 2017-0086804 on Mar. 30, 2017.
Final Office Action dated Apr. 24, 2019 in U.S. Appl. No. 15/277,542, filed Sep. 27, 2016 published as 2017-0086804 on Mar. 30, 2017.
Extended European Search Report dated May 13, 2019 in European Patent Application No. EP16850451.2 based on International Patent Application PCT/IB2016/001498 filed: Sep. 27, 2016 and published as: EP3355803 on Aug. 8, 2018.
Bountouris et al., "Endovascular aneurysm repair with Fascia suture technique: short and mid-term results," Int Angiol, Epub Nov. 10, 2015.
Fisher, "The Fascia Suture Technique: This Late Bloomer Could Become a Winner," J. Endovasc Ther, 2012, 19:397-399.
Freitas et al., "The use of closure devices in peripheral endovascular interventions: The Leipzig real-world report," Journal of The American College of Cardiology, TCT Abstracts/Vascular Access and Intervention—Femoral (includes closure devices) Abstract TCT-842, p. B245, Saturday, Sep. 13, 2014, 5:00 PM-7:00 PM.
Harrison et al., "Fascial Closure Following Percutaneous Endovascular Aneurysm Repair," Eur J Vasc Endovasc Surg (2011) 41, 346-349.
Larzon et al., "Editor's Choice—A Randomized Controlled Trial of the Fascia Suture Technique Compared with a Suture-mediated Closure Device for Femoral Arterial Closure after Endovascular Aortic Repair," Eur J Vasc Endovasc Surg (Feb. 2015) 49, 166-173.
Larzon et al., "Fascia Suturing of Large Access Sites After Endovascular Treatment of Aortic Aneurysms and Dissections," J Endovasc Ther, 2006, 13:152-157.
Lee et al., "Midterm outcomes of femoral arteries after percutaneous endovascular aortic repair using the Preclose technique," J Vasc Surg, 2008: 47:919-923.
Mathisen et al., "Complication Rate of the Fascia Closure Technique in Endovascular Aneurysm Repair," J Endovasc Ther 2012; 19:392-396.
Montan et al., "Short- and Midterm Results of the Fascia Suture Technique for Closure of Femoral Artery Access Sites After Endovascular Aneurysm Repair," J Endovasc Ther, 2011; 18:789-796.
Nelson, "Closure and Arterial Access Conundrums" Presentation, Saturday Jun. 7, 2014, Society for Vascular Surgery, 2014 Vascular Annual Meeting, Boston, Jun. 5-7.
Wanhainen, A., "Invited Commentary, Commentary on 'A Randomized Controlled Trial of the Fascia Suture Technique Compared with a Suture-mediated Closure Device for Femoral Arterial Closure After Endovascular Aortic Repair'" Eur J Vasc Endovasc Surg (Feb. 2015) 49, 174-174.
International Search Report and Written Opinion dated Jan. 31, 2017 in International Application No. PCT/IB2016/001498 filed: Sep. 27, 2016.
International Search Report and Written Opinion dated Feb. 13, 2019 in International Application No. PCT/SE2018/051173 filed: Nov. 14, 2018.
International Search Report and Written Opinion dated Feb. 12, 2019 in International Application No. PCT/SE2018/051172 filed: Nov. 14, 2018.

(56) References Cited

OTHER PUBLICATIONS

Non Final Office Action dated Dec. 15, 2016 in U.S. Appl. No. 15/291,991, filed Oct. 12, 2016, published as US-2017/0086807 on Mar. 30, 2017.
Notice of Allowance dated May 12, 2017 in U.S. Appl. No. 15/291,991, filed Oct. 12, 2016, published as US-2017/0086807 on Mar. 30, 2017.
Notice of Allowance dated Nov. 20, 2018 in U.S. Appl. No. 15/611,665, filed Jun. 1, 2017, published as: 2017-0265848 on Sep. 21, 2017.
Notice of Allowance dated Sep. 19, 2018 in U.S. Appl. No. 15/611,665, filed Jun. 1, 2017, published as: 2017-0265848 on Sep. 21, 2017.
Final Office Action dated Jan. 10, 2018 in U.S. Appl. No. 15/611,665, filed Jun. 1, 2017, published as: 2017-0265848 on Sep. 21, 2017.
Non-Final Office Action dated Aug. 9, 2017 in U.S. Appl. No. 15/611,665, filed Jun. 1, 2017, published as: 2017-0265848 on Sep. 21, 2017.
Non-Final Office Action dated Aug. 30, 2018 in U.S. Appl. No. 15/277,542, filed Sep. 27, 2016 published as 2017-0086804 on Mar. 30, 2017.
Non-Final Office Action dated Feb. 8, 2021 in U.S. Appl. No. 16/190,694, filed Nov. 14, 2018 published as: 2019-0142403 on: May 16, 2019.
Invitation to Pay Additional Fees dated Jan. 25, 2021 in International Application No. PCT/US2020/061117 filed: Nov. 18, 2020.
International Search Report and Written Opinion dated Jan. 28, 2020 in International Application No. PCT/SE2018/051041 filed: Oct. 23, 2019.
International Search Report and Written Opinion dated Mar. 26, 2021 in International Application No. PCT/US2020/061117 filed: Nov. 18, 2020.
Final Office Action dated Aug. 4, 2021 in U.S. Appl. No. 16/190,694, filed Nov. 14, 2018 and published as: 2019/0142403 on: May 16, 2019.

\* cited by examiner

COLLAPSIBLE TUBE FOR HEMOSTASIS

RELATED APPLICATIONS

This application claims priority from U.S. Provisional Patent Application Ser. No. 62/587,341, filed on Nov. 16, 2017, by Thomas Larzon et al. titled "Suture Tube", which is incorporated by reference herein in its entirety.

BACKGROUND

In many percutaneous cardiovascular procedures, a catheter is inserted into an artery, such as the femoral artery, through a percutaneous vascular access. The catheter may be inserted, typically over a guidewire, directly into an artery (a "bareback" procedure), or the catheter may be inserted through a vascular introducer. When the procedure is complete, the physician removes the catheter and then removes the introducer from the vessel (if one was used). The physician then must prevent or limit the amount of blood that leaks through the vascular access. Physicians currently use a number of methods to close the vascular access, such as localized external compression, suture-mediated closure devices, plugs, gels, foams and similar materials.

However, such closure procedures may be time consuming, and may consume a significant portion of the time of the procedure. In addition, existing methods are associated with complications such as hematoma or thromboses. Still further, some of such procedures, particularly suture-mediated closure devices, are known to have high failure rates in the presence of common vascular disease such as atherosclerosis and calcification.

SUMMARY

Some embodiments of a vascular closure device may include a housing including an elongate configuration with an axial length greater than a transverse dimension thereof, a proximal end, a distal end and a distal section. The vascular closure device may further include a plurality of anchor deployers configured to extend from the distal section of the housing. Each of the anchor deployers may include a deployment rod which is slidably disposed relative to the housing and which includes an elongate resilient configuration and a distal end that extends distally and radially outward from the distal section of the housing. Each anchor deployer may also include an anchor which is removably secured to the distal end of the deployment rod and which is configured to penetrate tissue in a distal direction and optionally prevent tissue penetration in a proximal direction. Each of the anchor deployers may also include a filament that may be slidably disposed within the housing and have a distal end which is secured to the anchor. A collapsible tube may be disposed over and optionally secured to a distal section of the filament proximal of and adjacent to the anchor. In some cases, the collapsible tube may include an elongate configuration having an axial length greater than a transverse dimension thereof and a wall structure that is configured to shorten in an axial length and radially expand upon axial compression. In some instances, the respective filaments of the plurality of anchor deployers may be slidably disposed within the housing adjacent each other at the distal section of the housing.

Some embodiments of a method of preventing blood leakage from a closure site of a passage in a tissue layer may include disposing a distal end of a housing of a vascular closure device to a position adjacent the passage in the tissue layer. A plurality of anchor deployers may be deployed from a distal section of the housing in a distal and radially outward direction from the housing into the tissue layer in positions disposed about the passage in the tissue layer. The method may also include penetrating the tissue layer with the plurality of anchor deployers of the vascular closure device and extending each of the plurality of anchor deployers distally through the tissue layer until a proximal end of a collapsible tube of each of the plurality of anchor deployers extends distally beyond a lower surface of the tissue layer. Once so deployed, an anchor of each of the anchor deployers may be proximally retracted by proximally retracting a filament which is secured thereto. The method may also include axially compressing the collapsible tube of each of the plurality of anchor deployers between the respective anchor and lower surface of the tissue layer by applying tension to the filament which is secured to the anchor and which is disposed within an inner lumen of the collapsible tube. The collapsible tube may be axially compressed until the collapsible tube shortens in axial length and expands in an outward radial direction adjacent the passage. Tension may also be applied to the filaments from the distal section of the housing to reduce a distance between the anchors drawing the anchors and adjacent tissue of the tissue layer radially inward so as to reduce the size of the passage in the tissue layer.

Some embodiments of a hemostasis device may include a housing having an elongate configuration with an axial length greater than a transverse dimension thereof, a proximal end, a distal end and a distal section. The hemostasis device may also include an anchor deployer having a deployment rod which is slidably disposed relative to the housing and which includes an elongate resilient configuration and a distal end that extends distally and radially outward from the distal section of the housing. An anchor may be removably secured to the distal end of the deployment rod and may be configured to penetrate tissue in a distal direction and optionally prevent tissue penetration in a proximal direction. A filament may be slidably disposed within the housing and may include a distal end which is secured to the anchor. A collapsible tube may be disposed over a distal section of the filament proximal of the anchor. The collapsible tube may include an elongate configuration having an axial length greater than a transverse dimension thereof and a wall structure that is configured to shorten in an axial orientation and expand radially outward upon axial compression.

Some embodiments of a method of preventing blood leakage from a tissue layer may include disposing a distal end of a housing of a hemostasis device at a position adjacent the tissue layer and deploying an anchor deployer from a distal section of the housing in a distal direction from the housing into the tissue layer. The method may also include penetrating the tissue layer with the anchor deployer and extending the anchor deployer distally through the tissue layer until a proximal end of a collapsible tube of the anchor deployer extends distally beyond a lower surface of the tissue layer. Once so deployed, an anchor of the anchor deployer may be proximally retracted by proximally retracting a filament which is secured thereto thus axially compressing the collapsible tube between the anchor and lower surface of the tissue layer by applying tension to the filament which is secured to the anchor and which is disposed within an inner lumen of the collapsible tube. The collapsible tube may be axially compressed until the collapsible tube shortens in axial length and expands in an outward radial direction.

Certain embodiments are described further in the following description, examples, claims and drawings. These features of embodiments will become more apparent from the following detailed description when taken in conjunction with the accompanying exemplary drawings.

BRIEF DESCRIPTION OF THE DRAWINGS

FIG. 9AA is a transverse cross section of the proximal section of the anchor deployer embodiment of FIG. 9A taken along lines 9AA-9AA of FIG. 9A.

The drawings are intended to illustrate certain exemplary embodiments and are not limiting. For clarity and ease of illustration, the drawings may not be made to scale, and in some instances, various aspects may be shown exaggerated or enlarged to facilitate an understanding of particular embodiments.

DETAILED DESCRIPTION

After a minimally invasive vascular procedure, a hole in the form of an access passage or the like may be left in a major vessel or other surgical target of interest at an access site that may need to be closed. Methods for percutaneous closure of such a hole may include remote suturing of the vessel, plugging the hole, and remote suturing of the fascia adjacent to the vessel. Certain device and method embodiments discussed herein are directed to mechanical closure of an access passage in the fascia tissue layer adjacent to an access hole in a vessel such as an artery or vein of a patient while minimizing blood leakage from the closure site. Certain device and method embodiments discussed herein may also be directed to mechanical closure of an access passage in the fascia tissue layer adjacent any other bodily structure that may require hemostasis including an abdominal cavity of a patient. Such device and method embodiments may be appropriate for any surgical procedure in which access is required via dissection of a fascia layer or any other tissue layer adjacent a surgical site of interest within the patient's body. Some of these embodiments may also be applicable to direct closure of an arterial wall in some instances. Some vascular closure device and method embodiments discussed herein may provide a robust and easy-to-use device for closing a vascular access hole after a minimally invasive procedure. In some cases, vascular closure device embodiments discussed herein may be useful for closing large vascular access holes. In addition, certain vascular closure device and method embodiments are discussed in U.S. patent application Ser. No. 15/277,542, filed Sep. 27, 2016, by Thomas Larzon, et al., entitled VASCULAR CLOSURE DEVICE, which is incorporated by reference in its entirety.

Figure 1:
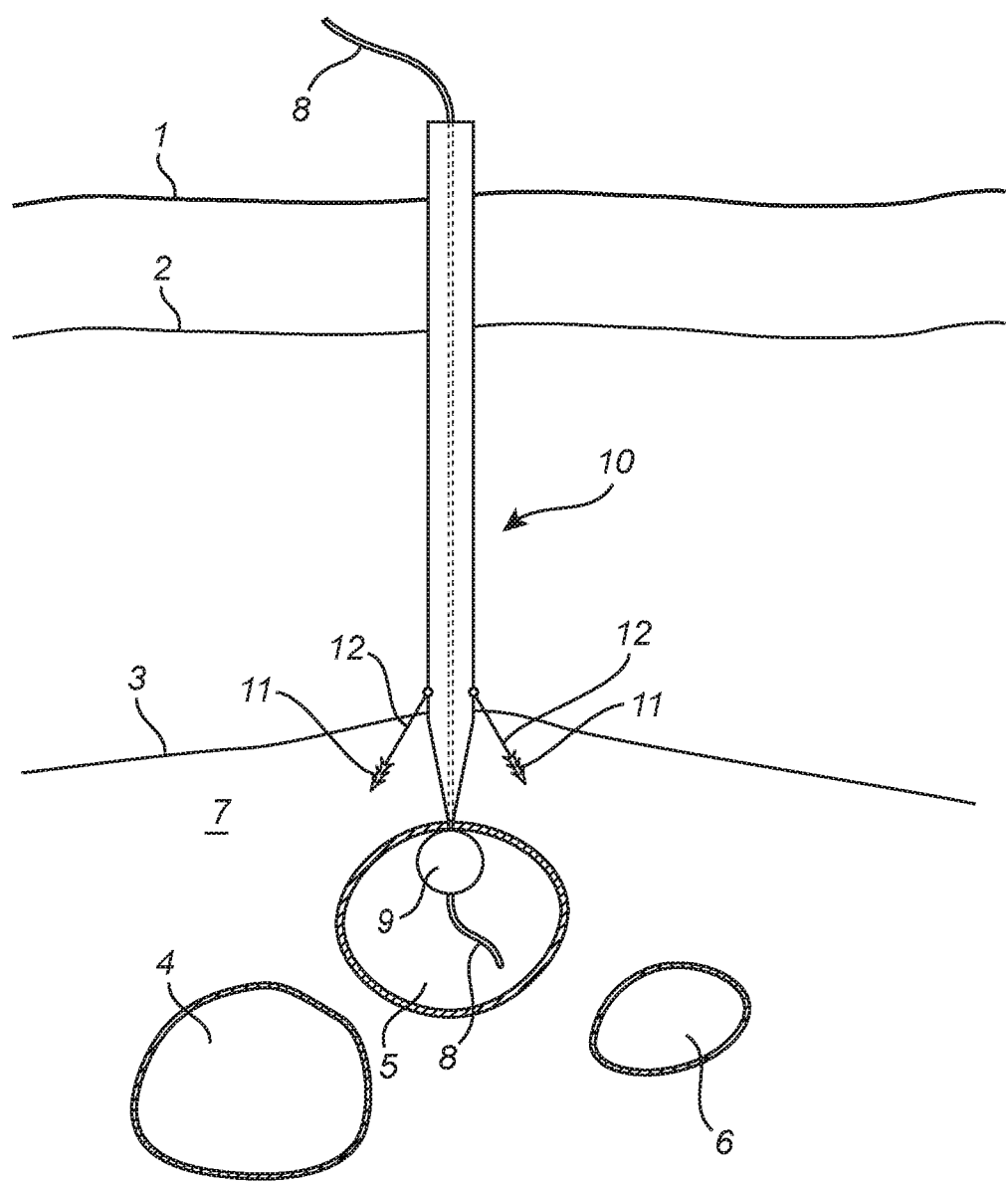
FIG. 1 schematically exemplifies a first embodiment of a vascular closure device.

The following discussion of the device and method embodiments of FIGS. 1-4B is directed generally to closure of a vascular access passage as well as axial positioning of certain portions of vascular closure device embodiments during such a closure procedure. Such axial positioning devices and methods may be applied to and used with any appropriate vascular closure device or method of embodiment discussed herein. Turning now to the drawings, and to FIG. 1 in particular, an embodiment of a vascular closure device 10 is introduced percutaneously over a guide wire 8 into a blood vessel/artery 5, through the skin 1 and the fascia lata 2 of a patient. An optional anvil member 9 may be arranged inside the blood vessel 5 to create a reference point along an axial orientation to the engagement members 11 and/or for controlling bleeding from an inner lumen of the artery 5. The engagement members 11 may then be placed and released through the vascular closure device 10 and may attach to fascia tissue 3 proximate to the blood vessel 5 and may involve the fascia membrane 3 (fascia iliacus), but, in some instances, not a wall 22 of the blood vessel 5. The engagement members 11 may for example be pushed out of the vascular closure device 10 and into the fascia membrane 3 using deployment members provided as pusher rods 12 arranged in independent lumens provided with the vascular closure device 10, for example through a pusher assembly in a common lumen that simultaneously deploys all engagement members 11, through a spring-loaded mechanism or the like. For some embodiments, the engagement members 11 may be connected with a single filament such as a suture or a plurality of filaments or sutures 13. In FIG. 1 there is further shown a femoral vein 4, a femoral nerve 6 and adjacent/interstitial tissues 7.

Figure 2A:
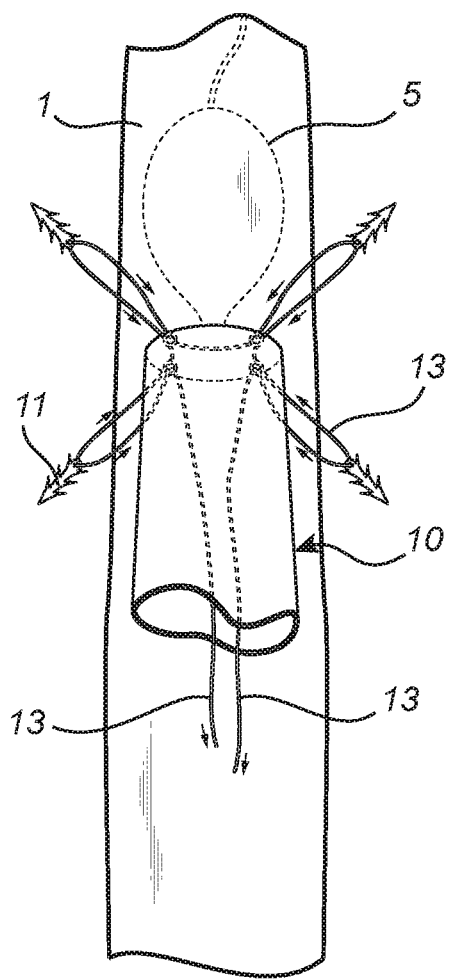
FIGS. 2A and 2B show the creation of a tissue lock using the vascular closure device.
Figure 2B:
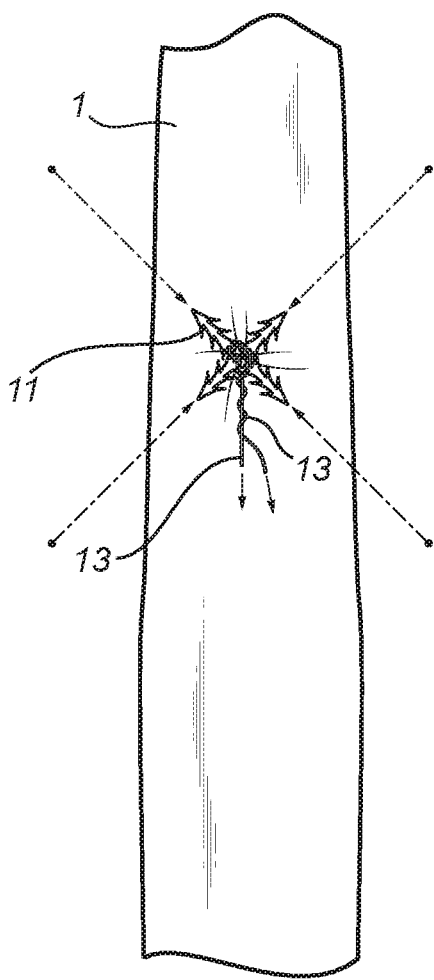

With further reference to FIGS. 2A and 2B, the suture 13 may for example be routed through each of the engagement members 11 in sequence. In particular, one suture 13 may be looped through each of the engagement members 11 in sequence, or a separate suture 13 may be attached to each engagement member 11. The tissue, e.g. fascia membrane 3, may then pulled together in a radially inward direction towards an access passage in the fascia layer 3 with the suture 13 connected to the engagement members 11. When pulled together, the tissue/fascia membrane 3 is tightened towards the center and the access passage therethrough and may then create a tissue lock, thereby indirectly sealing the access hole in the artery 5. That is, a distance between the initial position of the engagement members 11 and a distance between the engagement members once the engagement members 11 have been moved radially inward towards each other is thereby reduced. When tightening the fascia membrane 3 the anvil member 9 may be removed from the artery 5.

Figure 2C:
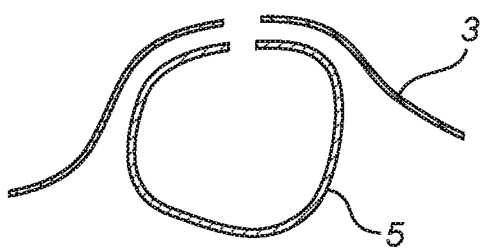
FIGS. 2C and 2D illustrate a closure sequence for treatment of an unwanted passage through a wall of a blood vessel.
Figure 2D:
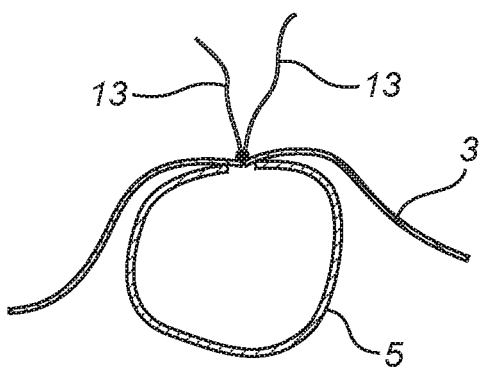

Referring to FIGS. 2C and 2D, an embodiment of a vascular closure sequence is shown whereby a passage through a wall 22 of the vessel 5 such as the blood vessel shown is treated such that leakage of blood from the interior volume of the blood vessel (not shown) is slowed or stopped to a clinically acceptable degree. As seen in FIG. 2C, a passage in the wall of the blood vessel, specifically, the femoral artery 5, is disposed in general alignment with a passage through the fascia tissue layer 3 disposed proximate to an outer surface of the femoral artery 5. For this particular exemplary embodiment, the tissue layer disposed outside of and proximate to the outer surface of the femoral artery 5 is the fascia iliacus 3. For purposes of this general discussion, the phrase "in general alignment" as applied to the respective passages may mean at least that an appropriately sized elongate device such as a catheter or sheath may pass through both passages without significant relative lateral displacement between the tissue 3 and artery 5.

In addition, in some cases, the tissue layer 3 may be disposed sufficiently proximate the outside surface of the blood vessel 5 such that gathering and approximation of the fascia tissue 3 which is disposed about the passage through the tissue 3 so as to close the passage through the tissue/fascia membrane 3 and form a tissue lock is sufficient to tighten and displace the closed gathered tissue/fascia membrane 3 against the outer surface of the artery 5 which is adjacent the passage through the artery 5 as shown in FIG. 2D.

When the gathered tissue 3 has been displaced and deflected so as to be disposed against the passage of the artery 5 and wall of the artery 5 disposed about the passage in the artery 5, this mechanical approximation will typically be sufficient in order to achieve a clinically sufficient slowing or stoppage of blood leakage from the passage in the artery 5 in order to permit closure of an access site through the patient's skin 1 adjacent the passages. In some instances, an inner surface of the tissue layer 3 disposed proximate to the outer surface of the blood vessel 5 may be separated from the outer surface of the blood vessel in the region of the respective passages therethrough by a distance of up to about 10 mm, more specifically, up to about 5 mm.

Figure 3A:
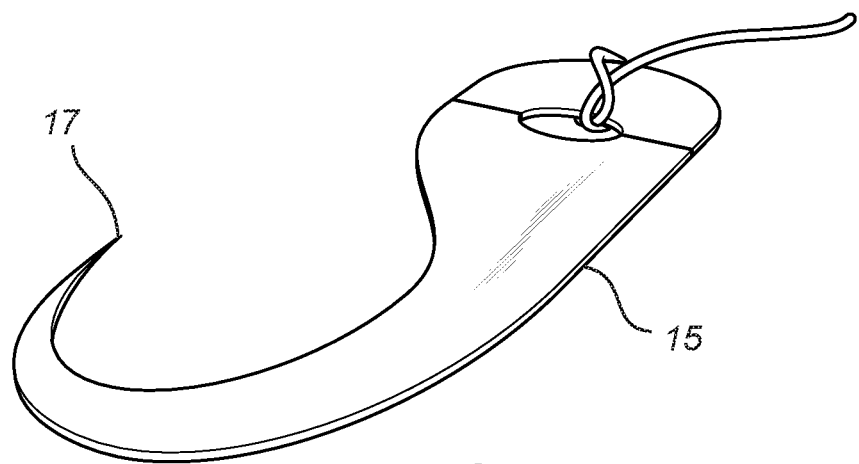
FIGS. 3A and 3B illustrate an engagement member, exemplified as an anchor element.
Figure 3B:
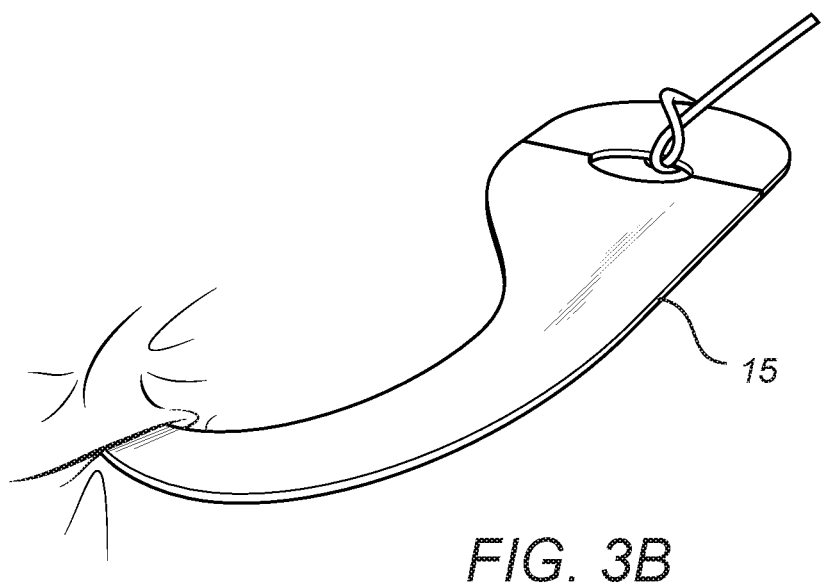

With further reference to FIGS. 3A and 3B, there is conceptually illustrated an engagement member, exemplified as an anchor element 15. In FIG. 3A, the anchor element 15 is shown as initially deployed, so that it slides easily in the direction away from a deployment point. Note that the deployment point may optionally be deflected toward the tissue/fascia membrane 3 to promote engagement. FIG. 3B shows the anchor element 15 after motion has been reversed toward the deployment point, and the anchor element 15 has embedded into the tissue/fascia membrane 3. That is, a tip 17 of the anchors element 15 is in one embodiment hook-shaped, so that it easily slides outward without engaging the tissue/fascia membrane 3. However, once the anchor element 15 is retracted, at least the tip 17 of the anchor element 15 is adapted to mechanically engage with the tissue/fascia membrane 3.

Figure 4A:
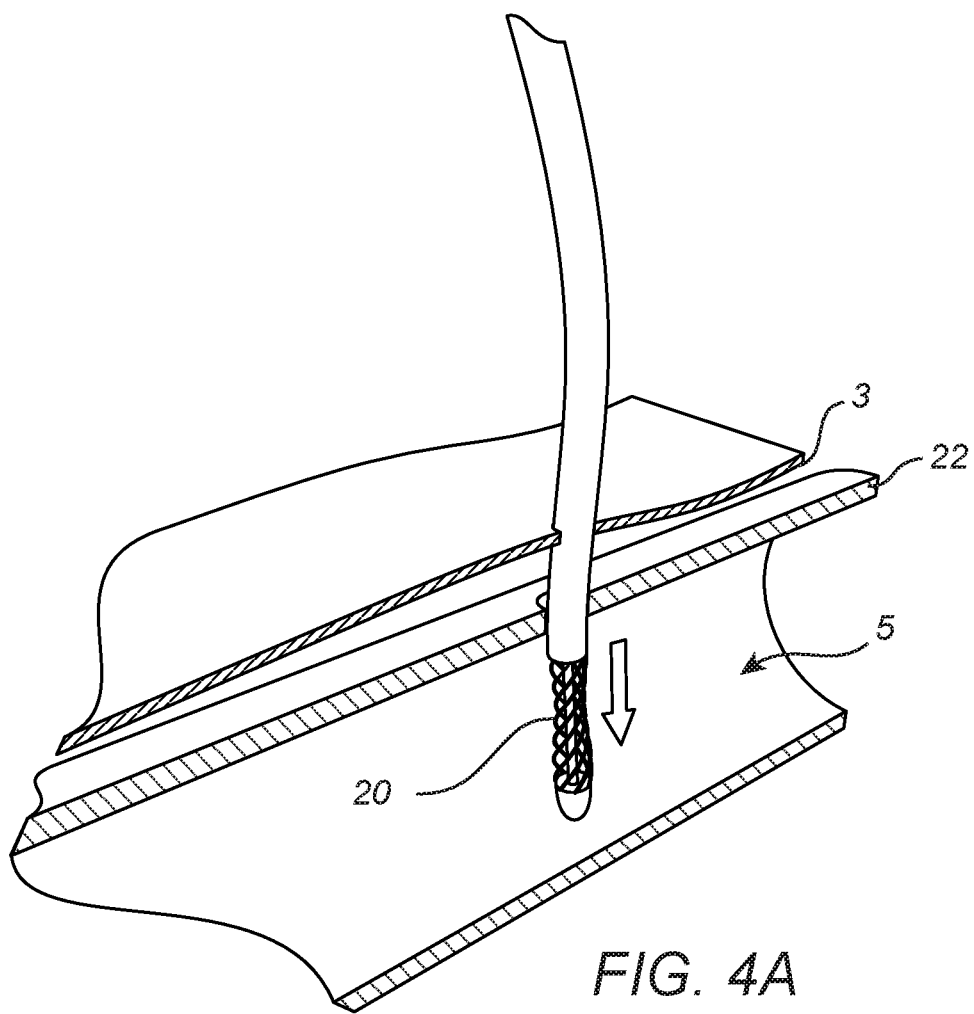
FIGS. 4A and 4B illustrate the operation of an anvil member that functions as a deployable positioning feature.
Figure 4B:
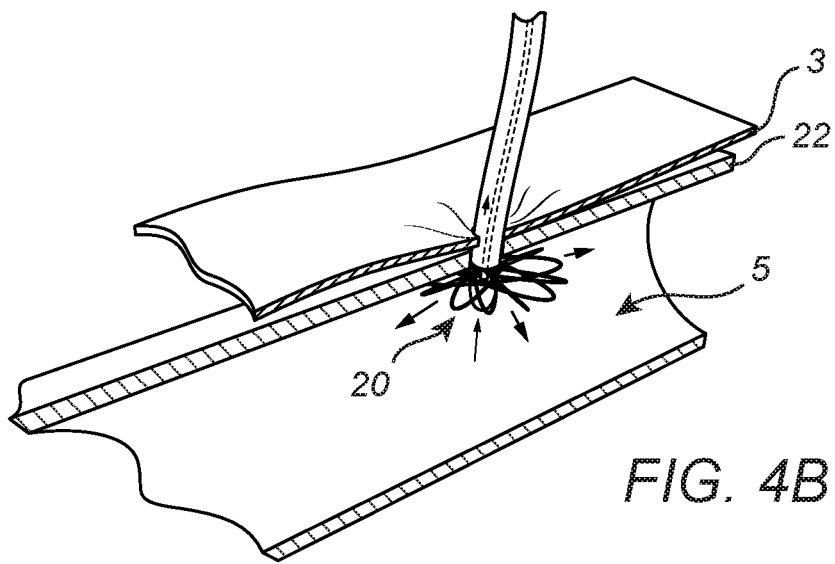

FIGS. 4A and 4B conceptually illustrate the operation of an anvil member exemplified as a deployable positioning feature 20. In FIG. 4A, deployable positioning feature 20 may be inserted through the wall 22 and into the interior volume of the blood vessel, such as the femoral artery 5. The deployable positioning feature 20 may be structured similar to an umbrella (using a mesh material), where the deployable positioning feature 20 in a radially collapsed form may be inserted into the artery 5. Once within the artery 5, with further reference to FIG. 4B, the deployable positioning feature 20 may be "unfolded" and radially expanded from the collapsed form such that a total surface area proximate to the longitudinal axis of the deployable positioning feature 20 is increased and thus may be retracted towards the interior wall of the artery 5. Accordingly, a reference point may be thereby established for further operation of the vascular closure device 10.

Some vascular closure device embodiments 24, as exemplified by the embodiments of FIGS. 5-15 which are discussed herein, may include a plurality of collapsible tubes 26 which may be utilized to hemostatically close, and prevent additional bleeding from, a vascular access site and target vessel 5 after a percutaneous cardiovascular procedure or the like has been performed. The vascular closure device 24 and method embodiments may include a plurality of anchor deployers 28 each of which may include a filament 30 which is secured to an anchor 32, a deployment rod 34, and a collapsible tube 26 which is disposed over and optionally secured to a distal end of the filament 30. Upon placement of a distal section of a housing 36 of the vascular closure device 24 near the vascular access site and deployment of the plurality of anchor deployers 28 into tissue 3, the anchors 32, filaments 30, and collapsible tubes 26 of the anchor deployers 28 may be manipulated such that fascia tissue layer 3 surrounding the access passage 38 (see FIG. 10) at the vascular access site and the collapsible tubes 26 provide hemostatic closure of the access passage 38 and access hole 44 in the target artery 5 of the vascular access site. Such devices and procedures may also be applicable for use in the treatment of access passages disposed in any other suitable structures beneath a fascia layer 3 (or any other suitable tissue layer) including veins, such as the femoral vein 4, abdominal cavities, and the like. Some such vascular closure device embodiments may include about 2 anchor deployers 28 to about 8 anchor deployers 28, more specifically, about 3 anchor deployers 28 to about 5 anchor deployers 28.

The vascular closure device 24 may be placed within a vascular access passage 38 created during the percutaneous cardiovascular procedure in order to access a target vessel 5. The anchor deployers 28 may then be extended distally and radially outward via the deployment rods 34 from the vascular closure device 24 and though tissue, such as a fascia tissue layer 3, that is adjacent to both the vascular access channel 38 and the target vessel 5. The deployment rods 34 may then be proximally retracted into the housing 36 of the vascular closure device 24, and the filaments 30 may be proximally tensioned. In some instances, proximal tensioning of the filaments 30 may result in a reorientation of each respective anchor 32 secured thereto. The reorientation of each of the plurality of respective anchors 32 may then result in mechanical capture of adjacent tissue 3 by each anchor 32 upon tensioning of the filaments 30. In some cases, after tensioning, a proximal portion of each filament 30 may be slidably disposed within a filament grip such as the lock ring 40 disposed on a distal end 42 of the housing 36 of the vascular closure device 24. Once deployed from the distal end 42 of the housing 36, the lock ring 40 may act to secure the filaments 30 relative to each other and relative to the fascia tissue layer 3 after tensioning resulting in compression of tissue between each filament 30 and each of the respective anchors 32. Thus tensioning of the filaments 30 may result in compression of the tissue 3 surrounding the access passage 38 in the fascia tissue layer 3 and an adjacent the access hole 44 in the target vessel 5, with the compressed fascia tissue layer forming a tissue lock in the form of a hemostatic seal around the access passage 38 and the access hole 44 in the artery 5.

As the filaments 30 are proximally retracted a proximal portion 46 of each collapsible tube 26 disposed thereon may be mechanically captured and stopped by surrounding tissue 3, while the distal end 48 of each collapsible tube 26 remains secured to the distal end 48 of the filament 30. Thus, during retraction of the filaments 30, a compressive axial load may be applied to each collapsible tube 26 by the respective filaments 30 disposed therein, resulting in buckling of each collapsible tube 26 about the respective filament 30. The buckling of each collapsible tube 26 may result in a reduction in the axial length of the collapsible tube 26 and outward radial expansion of the diameter of the collapsible tube 26. Depending on the configuration of collapsible tube embodiments 26, axial buckling of the collapsible tubes 26 may occur in a random fashion or may be predetermined to occur in a regular sinusoidal fashion, such as in an accordion fashion, by preconditioning the collapsible tubes 26 with wrinkles, stiffening rings, uneven wall thicknesses, and/or any other suitable geometric feature such as periodic variation in radius along an axial length of the collapsible tubes 26.

Further, the collapsible tubes 26 may be constrained by the respective filaments 30 and lock ring 40 such that upon final tensioning of the filaments 30 the axially compressed collapsible tubes 26 surround the vascular access channel 38 and hole 44 in the target vessel 5 may thereby provide additional hemostasis to the closed access passage 38. Thus upon deployment the collapsible tubes 26 may reduce bleeding through puncture holes 50 created by the insertion of the anchor deployers 28, from the access passage hole 44 in the target vessel 5, and around the access passage 38 in the fascia tissue layer 3 or the like by mechanically blocking the flow of blood around the filaments 30, by promoting the clotting of blood about the vascular access site, or by some combination of these two mechanisms. In some instances, the radial expansion of the proximal portions 46 of the collapsible tubes 26 during tensioning of the filaments 30, as well as the axial collapse and radial expansion of the collapsible tubes 26 in general, may also allow the collapsible tubes 26 to serve as anchors that resist proximal displacement through the puncture holes 50 during tensioning. As such, vascular closure device embodiments 24 are envisioned that may function as discussed above without the use of anchors 32 that are configured to resist proximal displacement through punch holes 50 upon tensioning of the filaments 30.

Figure 15:
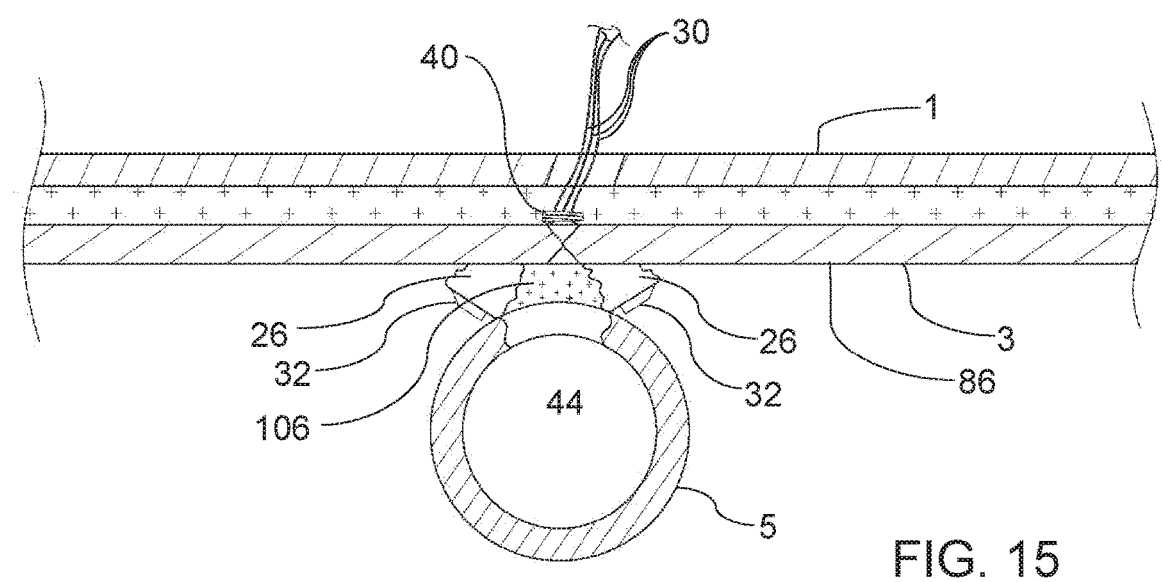
FIG. 15 shows the filaments of the vascular closure device in a tensioned state with the collapsible tubes in an axially compressed and radially expanded state after deployment of the lock ring and formation of thrombus between the compressed collapsible tubes.

For some embodiments, the collapsible tubes 26 may be fabricated from a thrombogenic material which actively promotes hemostasis such as collagen or any other suitable biologic or synthetic thrombogenic material. In some cases the collapsible tubes 26 may be fabricated from hydrophilic materials (such as a hydrogels and the like) which may expand upon interaction with fluids which are present within the tissue adjacent the collapsible tubes 26. Such expansion of collapsible tube embodiments 26 may provide additional thrombogenicity to the vascular access site and puncture holes 50. Thus the collapsible tubes 26 may achieve a hemostatic effect via a mechanical tampon or tamponade effect achieved by the buckling of the collapsible tubes 26 or by the biological\absorbent properties of the material(s) of the collapsible tubes 26 as shown in FIG. 15. Further collapsible tube embodiments 26 may be configured to easily slip over a respective filament 30, and may be configured with a relatively small outer transverse dimension such that the collapsible tube 26 does not interfere with or adversely affect the performance of the filament 30 during such a vascular closure procedure embodiment.

Figure 5:
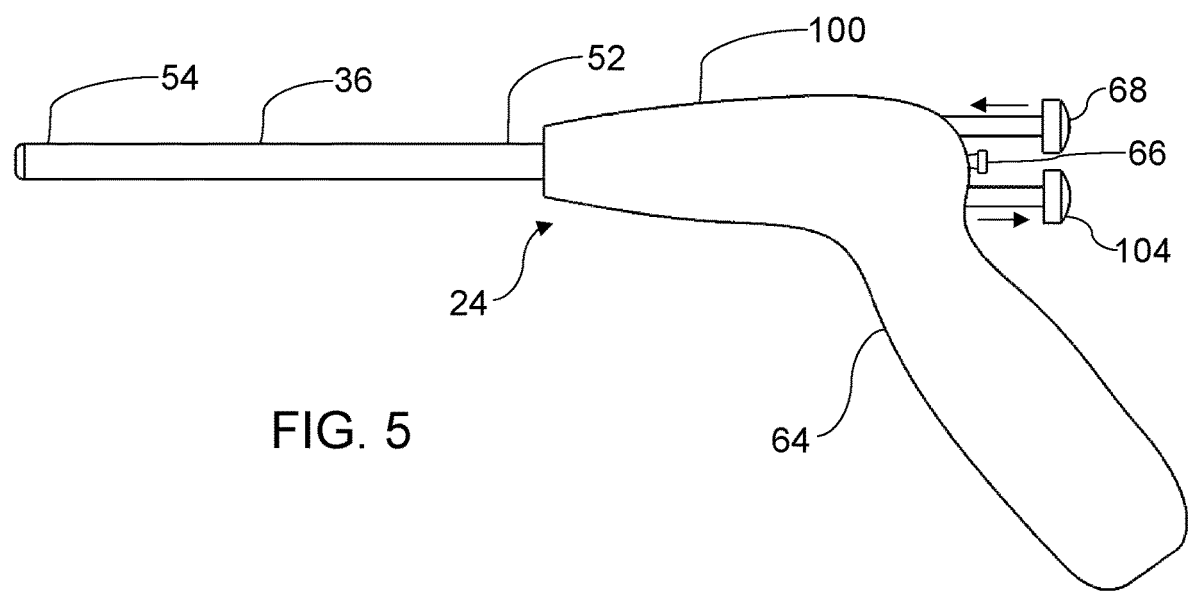
FIG. 5 is an elevation view of a vascular closure device embodiment.
Figure 6:
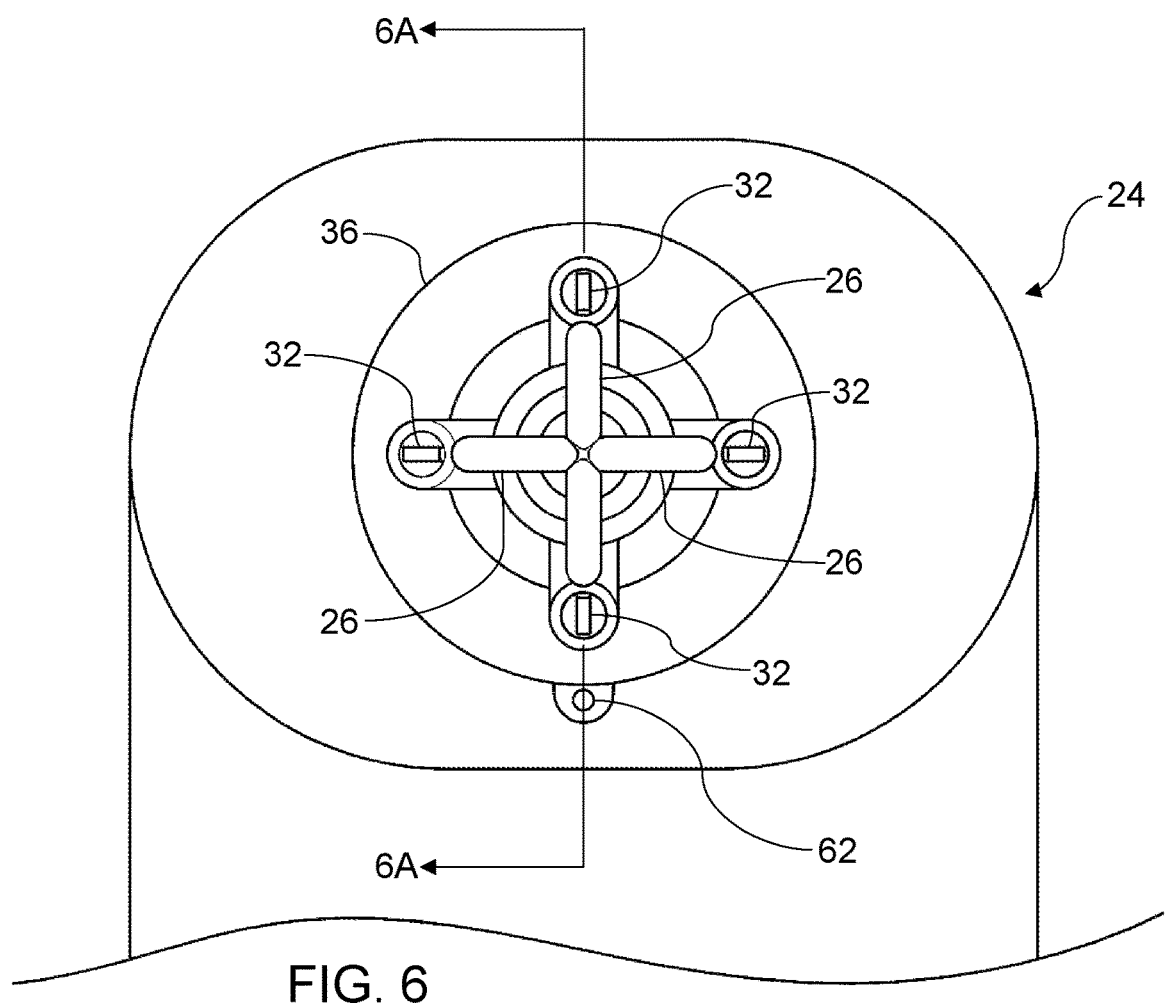
FIG. 6 is a front view of the vascular closure device of FIG. 5.
Figure 6A:
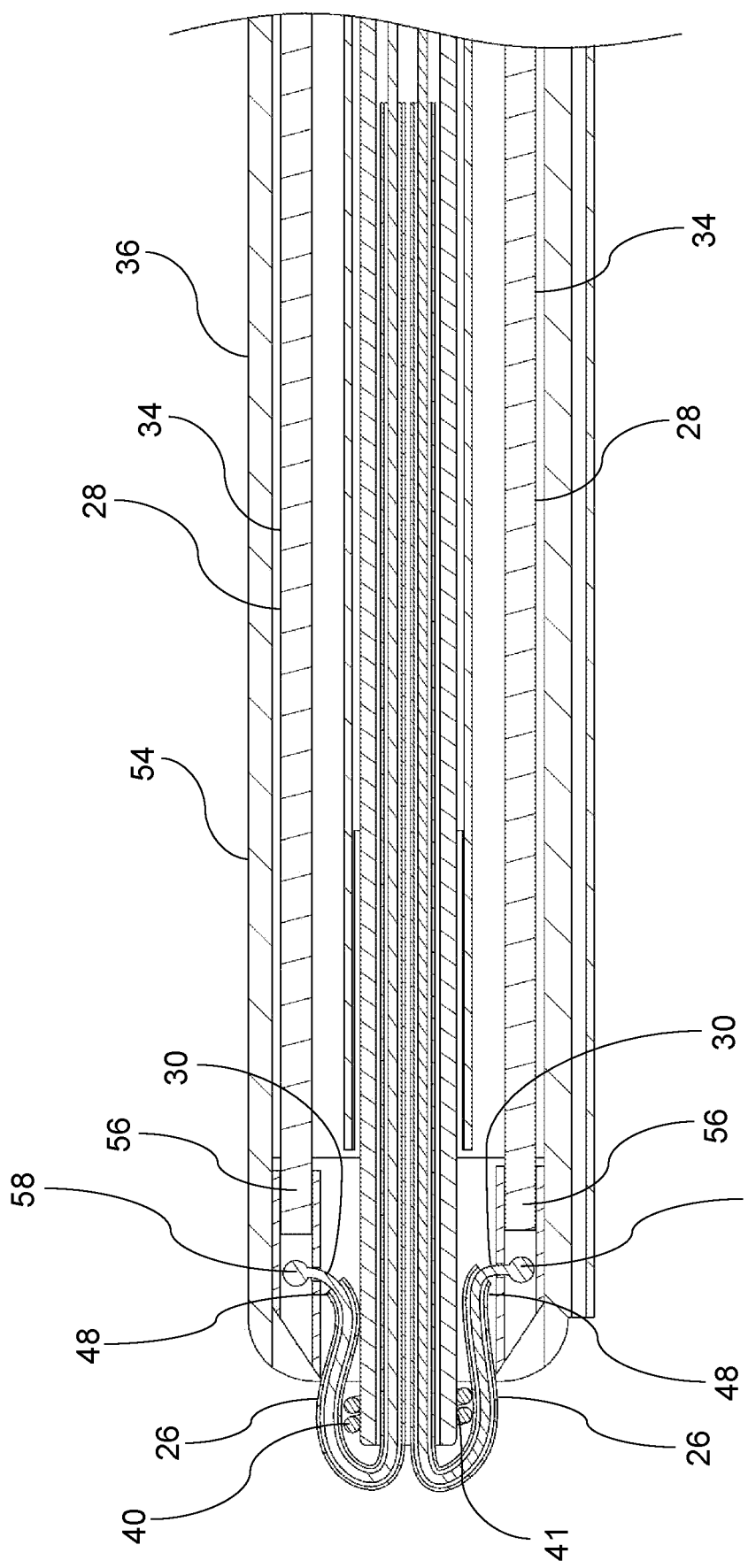
FIG. 6A is a section view of a distal portion of the housing of the vascular closure device of FIG. 6.

Referring to FIG. 5, the vascular closure device embodiment 24 includes a plurality of anchor deployers 28 and respective collapsible tubes 26, filaments 30 disposed therein and anchors 32. The vascular closure device 24 may include the housing 36 having an elongate configuration that is to say that an axial length of the housing 36 may be greater than a transverse dimension of the housing 36. The housing 36 may also include a proximal end 52, a distal end 42, and a distal section 54. The plurality of anchor deployers 28 may be suitably disposed within an interior volume of the housing 36 as shown in FIG. 6A. Each anchor deployer 28 may be configured to extend from the distal section 54 of the housing 36 and into target tissue during a vascular closure procedure. Each anchor deployer 28 may include the deployment rod 34, the anchor 32, the filament 30, and the collapsible tube 26 that may be disposed over the filament 30. Each deployment rod 34 may have an elongate resilient configuration, and may be slidably disposed relative to the housing 36 such that a distal end 56 of the deployment rod 34 may extend distally and radially outward from the distal section 54 of the housing 36 upon deployment of the respective anchor deployer 28.

Each anchor 32 of an anchor deployer 28 may be removably secured to the distal end 56 of the deployment rod 34 such that after penetration of the tissue layer 3 in a distal direction, the anchors 32 may slide off the distal end of the deployment rod 34 when the deployment rod 34 is proximally retracted. Each anchor 32 may be configured to penetrate tissue 3 in a distal direction and optionally prevent tissue penetration in a proximal direction. This configuration of the anchors 32 may be used to facilitate the deployment of the anchor deployers 28 distally into the target tissue 3 while allowing for the mechanical capture of the respective anchors 32 by surrounding tissue 3 and the associated collapsible tube 26 after retraction of the deployment rods 34 and proximal tensioning of the filaments 30.

Each anchor deployer 28 of the vascular closure device 24 may also include the filament 30 that may be slidably disposed within an inner lumen of the housing 36. The distal end 58 of the filament 30 may be secured to the anchor 30. In some instances, each filament 30 of the plurality of anchor deployers 28 may be slidably disposed within the housing 36 such that each filament 30 is disposed adjacent to another filament 30 at the distal section 54 of the housing 36 (see FIG. 6) and may optionally pass through a common lumen of the housing 36. Each anchor deployer 28 may also include a collapsible tube 26 that may be disposed over and secured to a distal section 60 of the respective filament 30, the distal section 60 of the filament 30 being disposed such that it is proximal of and adjacent to the anchor 30. In some cases, each collapsible tube 26 may have an elongate configuration such that an axial length of the collapsible tube 26 may be greater than a transverse dimension of the collapsible tube 26. Additionally, each collapsible tube 26 may have a wall structure that may be configured to shorten in axial length and radially expand upon axial compression. In some cases, the collapsible tubes 26 may be configured to buckle in an axial orientation upon axial compression of the collapsible tube 26.

Figure 10:
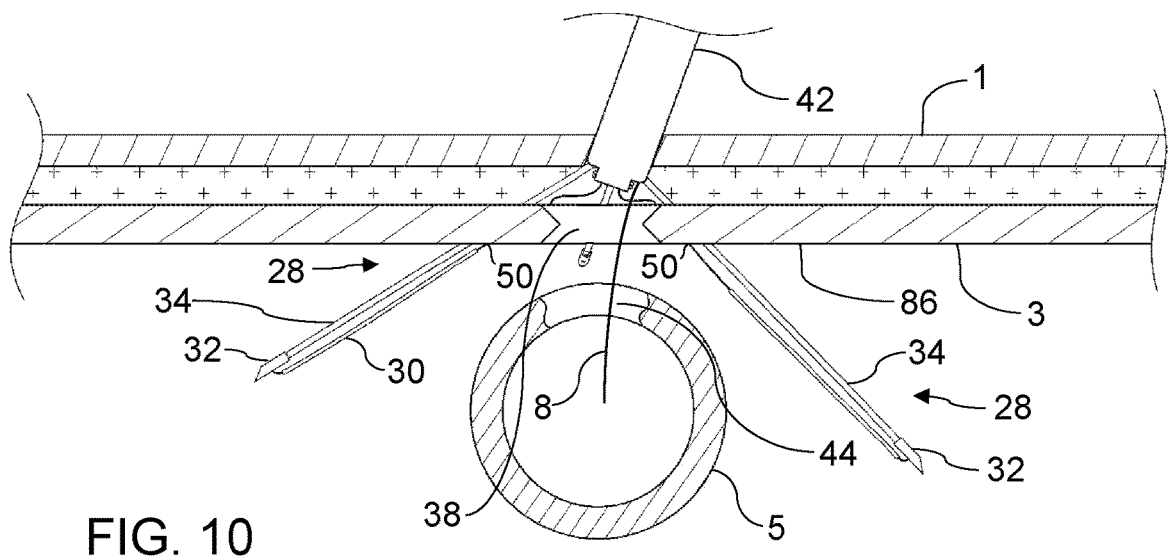
FIG. 10 is an elevation view in section of a distal section of a housing of the vascular closure device of FIG. 1 disposed adjacent an access passage in a fascia tissue layer with anchor deployers being deployed in the fascia tissue layer.
Figure 11:
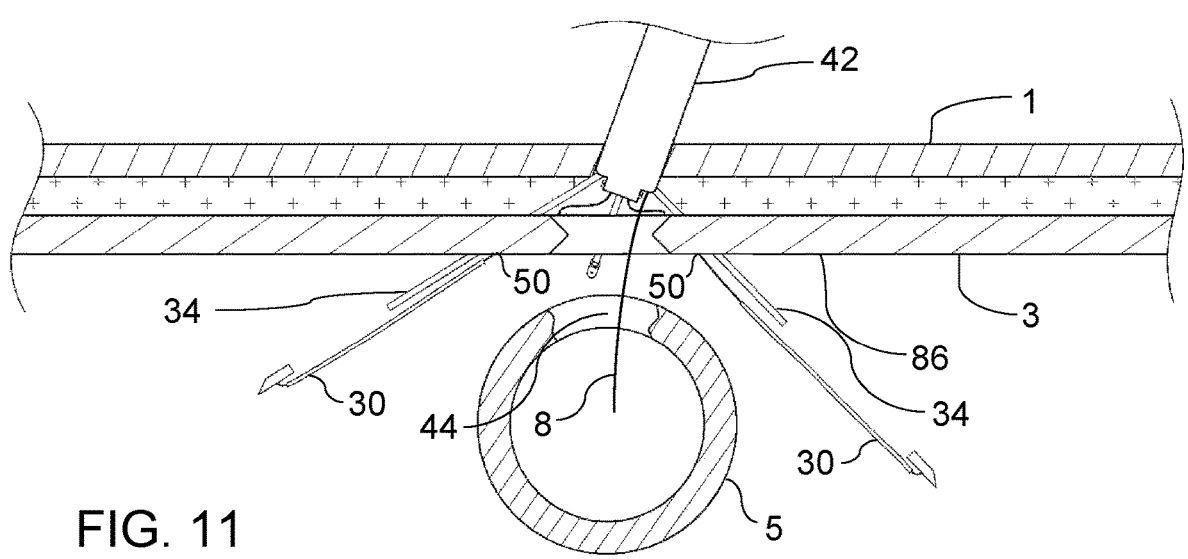
FIG. 11 shows deployment rods of the anchor deployers of the vascular closure device being proximally withdrawn back into the housing of the vascular closure device.
Figure 12:
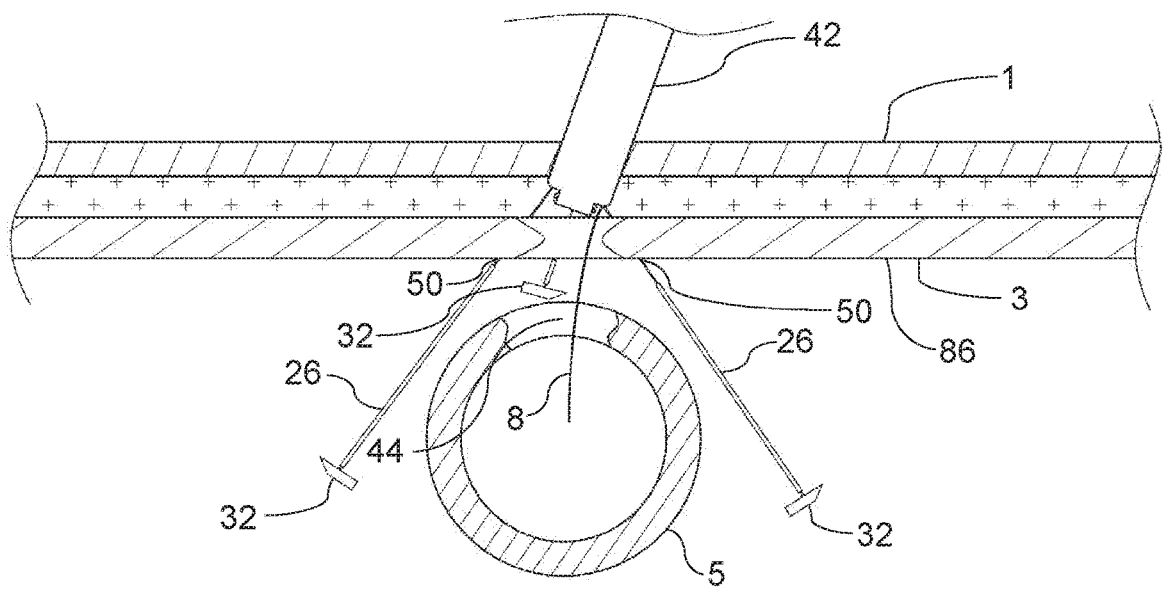
FIG. 12 shows the anchors, associated filaments and collapsible tubes of the vascular closure device disposed below the fascia tissue layer prior to tensioning of the filaments and compression of the collapsible tubes.

In some instances, the housing 36 may include a guidewire lumen 62 which may extend the axial length of the housing 36 from the proximal end 52 to the distal end 42 and which may include an eccentric lumen in some cases disposed towards an outside portion of the housing 36. The guide wire lumen 62 may be configured to allow for the passage of the guidewire 8 through the housing. In some cases, the guidewire 8 may remain within the target vessel 5 and within a vascular access channel 38 created during the percutaneous cardiovascular procedure. The guidewire lumen 62 disposed within the housing 36 of the vascular closure device 24 allows for the vascular closure device 24 to be coupled to the guidewire 62, thereby allowing for the tracking of the vascular closure device 24 along the guidewire 8 within the vascular access channel 38 as shown in FIGS. 10-12.

The vascular closure device 24 may also include a handle 64 that may be secured to the proximal end 52 of the housing 36. The handle 64 may be utilized in order to grasp and manipulate the vascular closure device 24 during a vascular closure procedure, and may include features which control the insertion of the anchor deployers 28 (via distal extension of the deployment rods 34), proximal retraction of the deployment rods 34, proximal tensioning of the filaments 30, and in some cases deployment of the lock ring 40 The handle 64 may include a Luer lock fitting 66 which is in fluid communication with the guidewire lumen 62 and which allows for access through the handle 64 to the guidewire lumen 62 which may be disposed within the housing 36.

The handle 64 may also include a rod pusher 68 that may be operatively coupled to each deployment rod 34. In some cases the rod pusher 68 may be operatively coupled to a proximal end of each deployment rod 34. The rod pusher 68 may be configured such that it can slide within the handle 64 both distally and proximally, thereby allowing for the rod pusher 68 to be utilized in order to distally extend or proximally retract each deployment rod 34 during a vascular closure procedure. The handle 64 may also include a filament tensioner 70 which may be operatively coupled to each filament 30 such that tension applied to the filament tensioner 70 in a proximal direction applies a corresponding proximal tension to the filaments 30. The filament tensioner 70 may be may be configured such that it can slide proximally within the handle 64, thereby allowing for the filament tensioner 70 to be utilized in order to proximally tension the filaments 30.

Upon deployment the collapsible tube embodiments 26 which are discussed herein may be utilized in order to reduce the chance of bleeding through puncture holes 50 created by the insertion of the anchor deployers 28, from the hole 44 in the target vessel 5, and the access passage 38 around the vascular access site by mechanically blocking the flow of blood around the filaments 30, by promoting the clotting of blood about the vascular access site, or by some combination of these two mechanisms. As such the collapsible tube embodiments 26 may be configured in order to facilitate buckling upon axial compression of the collapsible tube 26. In some cases, such axial buckling may lead to a shortening of the axial length of the collapsible tube embodiments 26 and an expansion outward in a radial direction of the collapsible tube 26 to create a larger transverse profile of the collapsible tube 26. Further, in some cases the collapsible tubes 26 may be fabricated from a material which may be thrombogenic such that the collapsible tubes 26 induce clotting, or from a material which absorbs fluids and expands in order to increase the volume of the collapsible tube 26 upon deployment.

Embodiments of collapsible tubes 26 are shown in FIGS. 7, 7A, 8, 9A, 9B, and 9C. Each collapsible tube embodiment 26 may have an elongated configuration wherein the axial length of the collapsible tube 26 may be greater than the transverse dimension of the axial tube. Each collapsible tube embodiment 26 which is discussed herein may optionally have an axial length of about 3 mm to about 15 mm, and an outer transverse dimension of about 0.5 mm to about 2 mm. In some instances, the collapsible tube embodiments 26 may be configured for ease of insertion during anchor deployer actuation, ease of collapsible tube wall structure bucking during tensioning of the filaments, mechanical stoppage against the fascia tissue layer 3 against which the collapsible tubes 26 are compressed during filament tensioning or any combination of these configurations.

Figure 7:
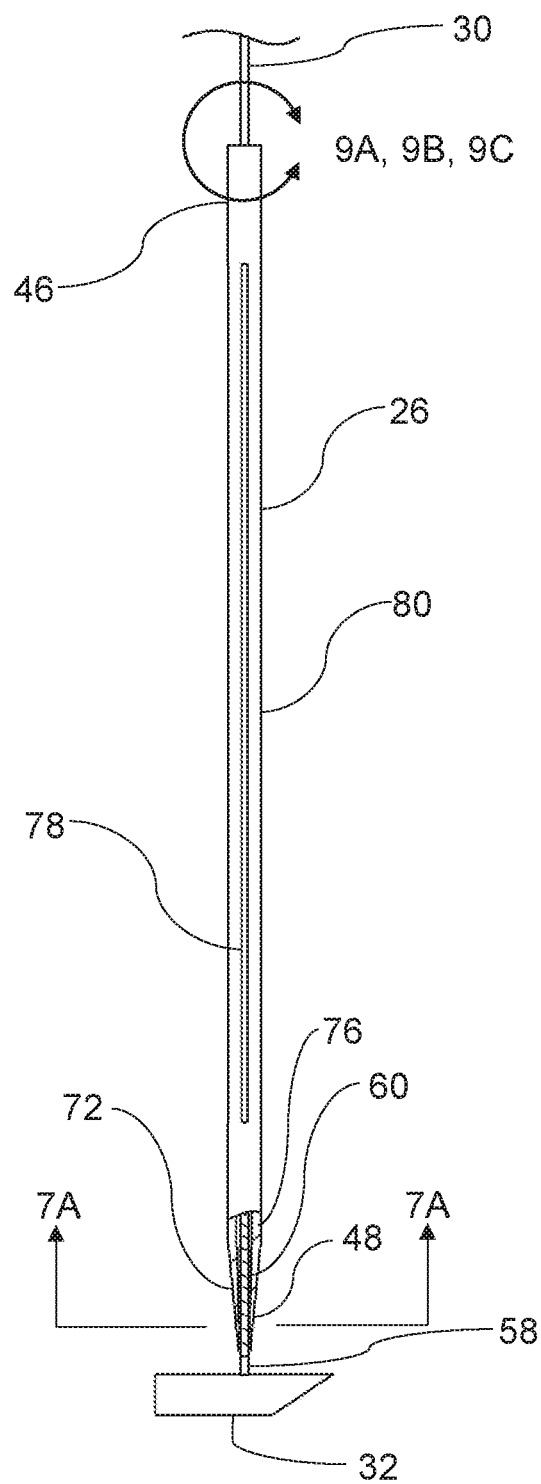
FIG. 7 shows an embodiment of an anchor deployer of the vascular closure device of FIG. 1.
Figure 7A:
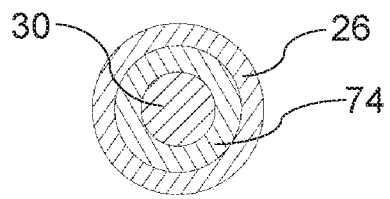
FIG. 7A is a transverse cross section view of the anchor deployer of FIG. 7 taken along lines 7A-7A of FIG. 7.
Figure 8:
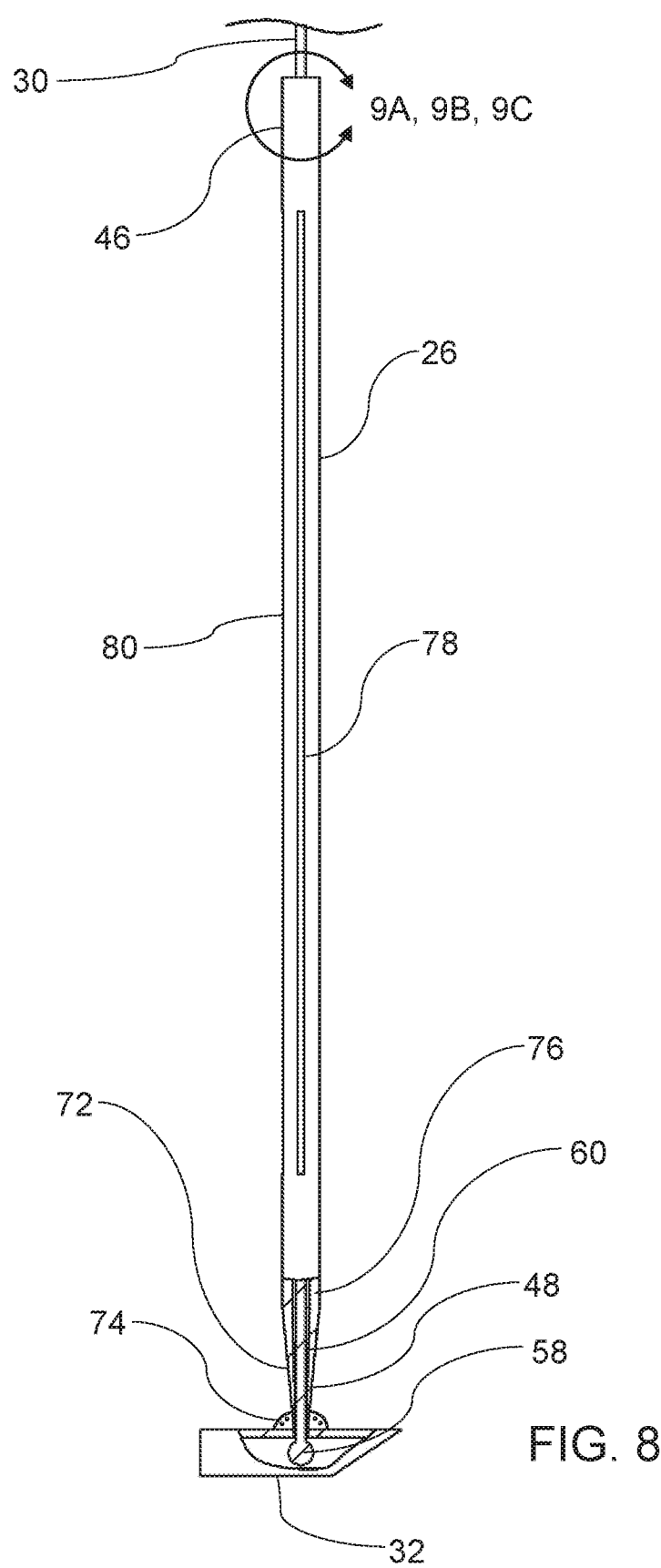
FIG. 8 shows an embodiment of an anchor deployer of the vascular closure device of FIG. 1.

FIG. 7 depicts a collapsible tube embodiment 26 having a distal section 72 which tapers distally to a reduced outer transverse dimension. The purpose of the distal section 72 which tapers is to facilitate the insertion of the collapsible tube 26 through a puncture hole 50 during distal deployment of the respective anchor deployer 28. In some cases, a distal end 48 of the collapsible tube 26 may be secured to the filament 30 in a position which is proximal of and adjacent to the anchor 32. In some cases, the collapsible tube 26 may be secured to the filament 30 with an adhesive 74 which may be disposed between an inner surface of the distal section 72 of the collapsible tube 26 and an outer surface of the filament 30 as shown in FIG. 7A. The adhesive 74 may be any suitable adhesive such as cyanoacrylate, UV-cured adhesive, or the like. In some cases, the collapsible tube 26 may be welded or fused to the filament 30 wherein material contained within the distal section 60 of the filament 30 may be thermally fused to material contained within the distal section 72 of the collapsible tube 26 such that the distal section 72 of the collapsible tube 26 is adjacent to the anchor 32 after the fusion process. In some instances, in order for the collapsible tube embodiments 26 to axially compress and radially expand properly when subject to axial compression, it may be desirable for the collapsible tubes 26 to be bonded or otherwise secured to the filament 30 only at the distal end of the filament 30 with the remainder of the collapsible tube 26 having an inner lumen sized to allow an inner surface of the inner lumen of the collapsible tube 26 to slide freely in an axial direction over an outer surface of the filament 30. For some embodiments, an axial length of the bond section between the filament 30 and the distal end of the collapsible tube 26 may be up to about 10 percent of an overall axial length of the collapsible tube 26. For some embodiments, the distal end 48 of the collapsible tube 26 may be secured directly to the anchor 32 as shown in FIG. 8. The distal end 48 of the collapsible tube 26 may be secured directly to the anchor 32 by the adhesive 74 such as cyanoacrylate, UV-cured adhesive, thermal bonding, welding, mechanical crimping or the like.

In some cases, the wall structure 76 of the collapsible tubes 26 may be modified in order to facilitate buckling of the collapsible tubes 26 upon proximal tensioning of the filaments. The collapsible tube embodiments 26 which are depicted in FIGS. 7 and 8 each incorporate at least one longitudinal slit 78 in a middle section 80 of the wall structure 76 of each collapsible tube 26. Each collapsible tube embodiment 26 which is discussed herein may include a plurality of longitudinal slits 78 within the wall 76 of the middle section 80, in some instances the longitudinal slits 78 may extend entirely through the wall 76 from an outside surface to an inside surface of the wall 76. In some other instances the longitudinal slits 78 may extend only partially through the wall 76 of the collapsible tube 26. For some embodiments discussed herein, each collapsible tube 26 may have from about 1 to about 5 longitudinal slits disposed within the wall structure 76 thereof. Additionally, an axial length of each longitudinal slit 78 may be from about 25 percent to about 75 percent of an axial length of the respective collapsible tube 26. As discussed above, such structures may be useful for effecting axial buckling of the collapsible tubes 26 in a predetermined regular sinusoidal fashion, such as in an accordion fashion.

As has been discussed above, materials that may be used for some embodiments of the collapsible tubes 26 may have thrombogenic or hydrophilic properties in order to reduce bleeding from the access passage 38 or through the puncture holes 50 created during the deployment of the anchor deployers 28. Some materials that may be used for the collapsible tube embodiments 26 that are discussed herein may be selected from the group consisting of polyurethane, polyethylene terephthalate (PET), polyetherether keytone PEEK, polytetrafluoroethylene (PTFE), acrylic, silicone, polypropylene, and polyester or the like. Some materials that may be used for the collapsible tube embodiments 26 that are discussed herein may include thrombogenic materials may include collagen, fibrin, fibrinogen, gelatin, polylactic acid (PLA), polyglycolic acid (PGA), alginate and fibronectin or the like. Some materials that may be used for the collapsible tube embodiments 26 that are discussed herein may include hydrogel materials which absorb fluids from surrounding tissue and expand. Hydrogel collapsible tube materials may include fibrin, collagen, gelatin, hyaluronic acid, alginate, agarose, poly(ethylene glycol), poly(acrylic acid), poly(vinyl alcohol), polypeptides, and poly(vinyl pyrrolidone). Further some materials that may be used for the collapsible tube embodiments 26 that are discussed herein may include biodegradable or bio-absorbable materials, such as poly(lactic acid), which may be absorbed by the surrounding tissue over time.

Figure 9A:
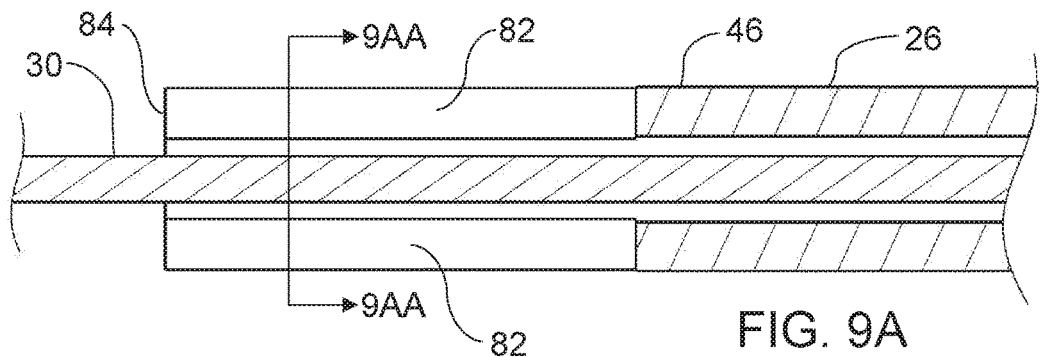
FIG. 9A is a section view of a proximal section of an anchor deployer embodiment.
Figure 9A:
Figure 9B:
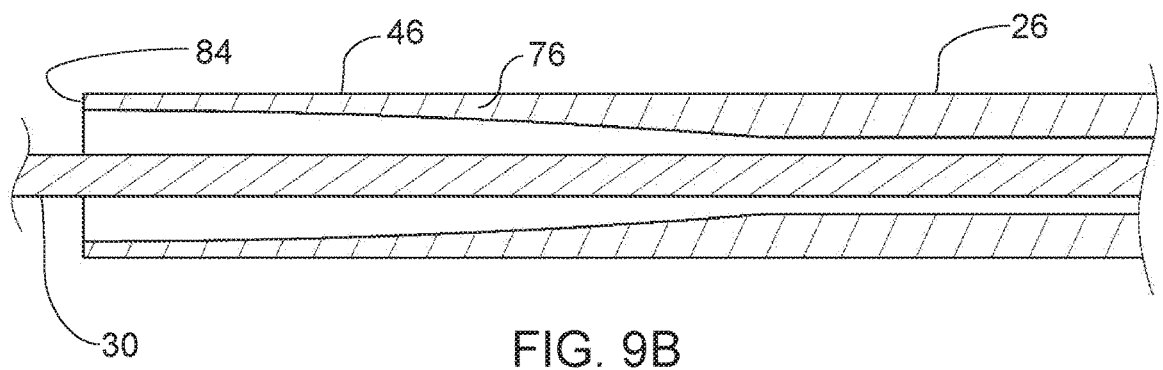
FIG. 9B is a section view of a proximal section of an anchor deployer embodiment.
Figure 9C:
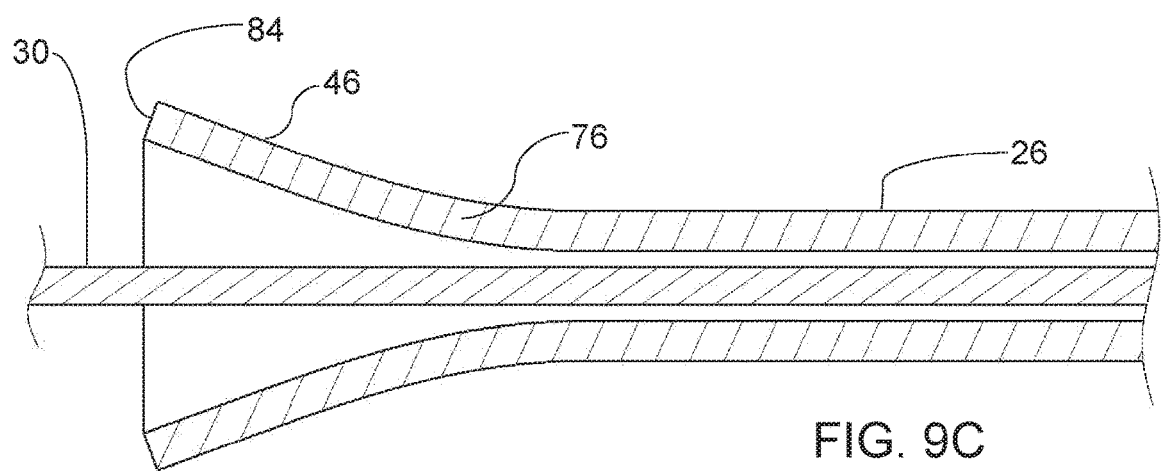
FIG. 9C is a section view of a proximal section of an anchor deployer embodiment.

In some instances, during proximal tensioning of the filaments 30 and axial compression of the collapsible tubes 26, it may be advantageous for a proximal section 46 of each collapsible tube 26 to be mechanically stopped in a proximal direction by surrounding tissue of a bottom surface of the fascia tissue layer 3 such that the collapsible tube 26 is not retracted proximally through the puncture hole 50 created during the deployment of the respective anchor deployer 28. FIGS. 9A, 9B, and 9C show collapsible tube embodiments 26 having proximal sections 46 which are configured to expand and be mechanically stopped in a proximal direction by a bottom surface of the fascia tissue layer 3 or any other surrounding tissue during proximal tensioning of the filaments 30.

In some instances, the proximal section 46 of a collapsible tube embodiment 26 may have at least one proximal slit 82 through the wall 76 of the collapsible tube 26, the proximal slit 82 extending distally from the proximal end 84 of the collapsible tube 26 as shown in FIGS. 9A and 9AA. In some cases, the proximal section 46 of the collapsible tube 26 may have about 1 to about 5 slits, and an axial length of each proximal slit 82 may be from about 1 mm to about 4 mm. During proximal tensioning of the filaments 30, the proximal slits 82 may allow for outward radial expansion of the proximal section 46 against the bottom surface of the fascia tissue layer 3 or any other adjacent tissue, with the result being the proximal section 46 being mechanically stopped in a proximal axial direction by the bottom surface of the fascia tissue layer 3 during tensioning of the filaments 30 and the proximal section 46 is prevented from being pulled through the puncture holes 50 back through the fascia tissue layer.

FIG. 9B depicts the proximal section 46 of a collapsible tube embodiment 26 wherein a wall thickness of the wall structure 76 of the collapsible tube 26 tapers to a reduced wall thickness from a position which is distal of the proximal end 84 of the collapsible tube 26 to a position at the proximal end 84 of the collapsible tube 26. During proximal tensioning of the filaments 30, the reduced wall thickness may facilitate outward radial expansion of proximal section 46 over a bottom surface of the fascia tissue layer 3 with the result being the proximal section 46 is mechanically stopped from proximal movement or being pulled back through the puncture hole 50 during tensioning of the filaments 30.

In some instances, the proximal section 46 of the collapsible tube embodiment 26 flares to a larger outer transverse dimension from a position which is distal of the proximal end 84 of the collapsible tube 26 to a position at the proximal end 84 of the collapsible tube 26. During proximal tensioning of the filaments 30, the flared expanded wall 76 allows for a wider distribution of compressive force by the proximal end 84 of the collapsible tube 26 against the bottom surface of the fascia tissue layer 3. Outward radial expansion of proximal section 46 may also be facilitated by the flared configuration. Such a flared proximal end configuration of the collapsible tube embodiment shown in FIG. 9C may be useful to mechanically stop the proximal end 84 of the collapsible tube 26 and prevent proximal movement of the proximal end 84 or the proximal end 84 from being pulled back through the puncture hole 50 during tensioning of the filaments 30.

Embodiments of the vascular closure device 24 may include any suitable configuration of the filaments 30 and or filament material including suture material. In some cases the suture material of the filaments 30 may be configured as a monolithic strand, and in some other cases the suture material may be braided. For some embodiments, bioabsorbable suture may be utilized. Further, in some cases, the suture material may be coated with any suitable coating such as a hydrophilic coating or an antimicrobial coating. In some instances, the size of the suture of some filament embodiments 30 may vary from U.S.P. #1 to U.S.P. #4 and may also include suture materials such as 2/0 suture to 3/0 suture, or other high strength filament 30 of the same or similar diameter. As discussed above, the collapsible tubes 26 may be configured to slide easily over the respective filament 30 and may also be configured with a minimal outer transverse dimension such that the collapsible tubes 26 do not interfere with the deployment of the anchor deployers 28. In some cases, the ratio of the outer transverse dimension of the collapsible tube 26 to an outer transverse dimension of the filament 30 may be from about 1.5:1 to about 4:1.

Some vascular closure device embodiments 24 may also include a filament grip feature that may be configured as the lock ring 40 and that may function to mechanically secure the filaments 30 in fixed relation to each other and the fascia tissue layer 3 after proximal tensioning and axial collapse of the collapsible tubes 26. In some cases the lock ring 40 may be disposed on the distal end 42 of the housing 36 as shown in FIG. 6A. The lock ring 40 is disposed adjacent and about the filaments 30 at the distal end 42 of the housing 36, and may be configured to compress and secure the filaments 30 relative to each other once deployed from the distal end 42 of the housing 36 so as to transition from an expanded state on the housing 36 to a self-contracting relaxed state with a compressive inward radial force on the filaments 30. For some embodiments the lock ring 40 may be configured as a self-retracting coil having a central lumen 41 which is disposed about the filaments 30. In some cases the lock ring 40 may be sized in order to allow free movement of the filaments 30 when the self-retracting coil is disposed in an expanded state. In turn the lock ring 40 may have an interior surface of the central lumen 41 that is sized and configured to compress the filaments 31 when in the lock ring 40 is disposed a retracted state as shown in FIG. 15.

As discussed above, the anchors 32 may act to mechanically capture surrounding tissue after deployment of the anchor deployers 28 and upon proximal tensioning of the filaments 30. In some cases the anchors 32 may optionally be sized and configured to present a surface area adjacent to the connection between the filament 30 and the anchor 32 that is wider than an outer transverse dimension of the collapsible tube which may prevent the filament 30 and anchor 32 from being pulled through the inner lumen of the collapsible tube 26 upon tensioning of the filaments 30 against the lower surface of the fascia tissue layer 3. In some instances the anchors 32 may be configured to rotate, pivot or expand after being deployed from the distal end 56 of the respective deployment rods 34. In some cases the anchors 32 may be formed from a hypo tube section which has an inclined sharpened end portion with the respective filament 30 secured to a mid-portion of the anchor 32. In some cases, the distal end of the filament 30 may be secured to the anchor 32 with adhesive, a knot, an enlarged distal portion of the filament 30 captured by a hole in the anchor 32 or the like.

FIGS. 10-15 depict a method for the deployment of the vascular closure device 24 into a vascular access site for closure of the access passage 38 in order to prevent blood leakage from the access hole 44 in the artery 5 of the vascular access site. As shown in FIG. 10, the distal end 42 of a housing 36 of the vascular closure device 24 may be disposed to a position adjacent the access passage 38 in the fascia tissue layer 3, as well as the deploying of a plurality of anchor deployers 28 from the distal section 54 of the housing 36 in a distal and radially outward direction from the housing 36 and into the tissue layer 3 in positions which are disposed about the access passage 38 in the fascia tissue layer 3. The plurality of anchor deployers 28 of the vascular closure device 24 are shown to be penetrating the tissue layer 3 and extending through the tissue layer 3 until a proximal end 84 of the collapsible tube 26 of each of the plurality of anchor deployers 28 extends distally beyond the lower surface 86 of the tissue layer 3. FIG. 11 depicts proximally withdrawing the deployment rods 34 of each of the plurality of anchor deployers 28 from respective anchors 32 and into the distal section 54 of the housing 36 of the vascular closure device 24.

Figure 13:
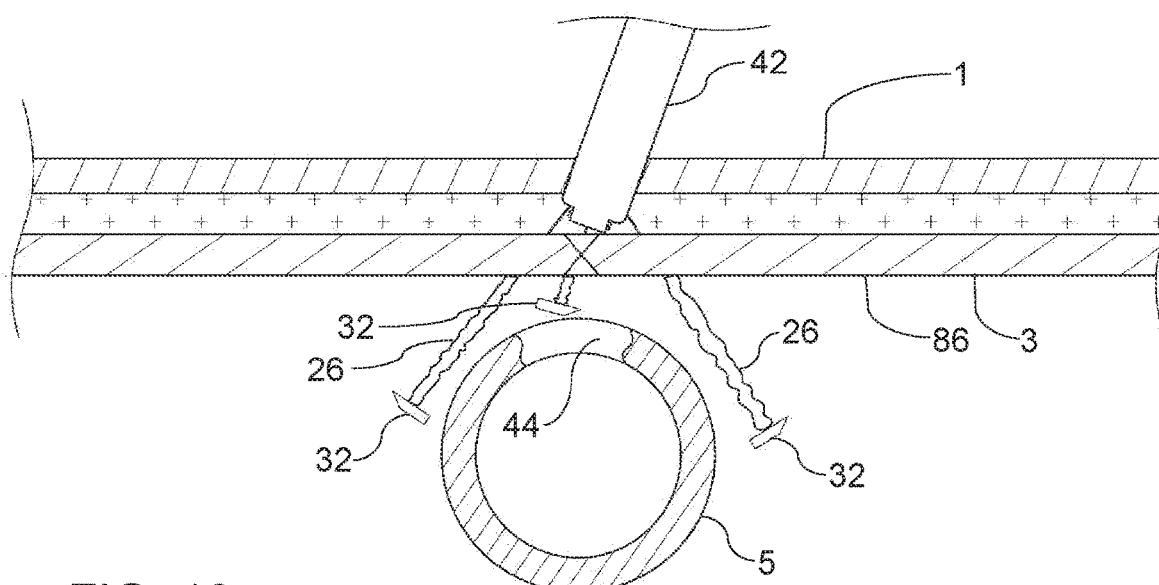
FIG. 13 illustrates tensioning of the filaments of the vascular closure device.
Figure 14:
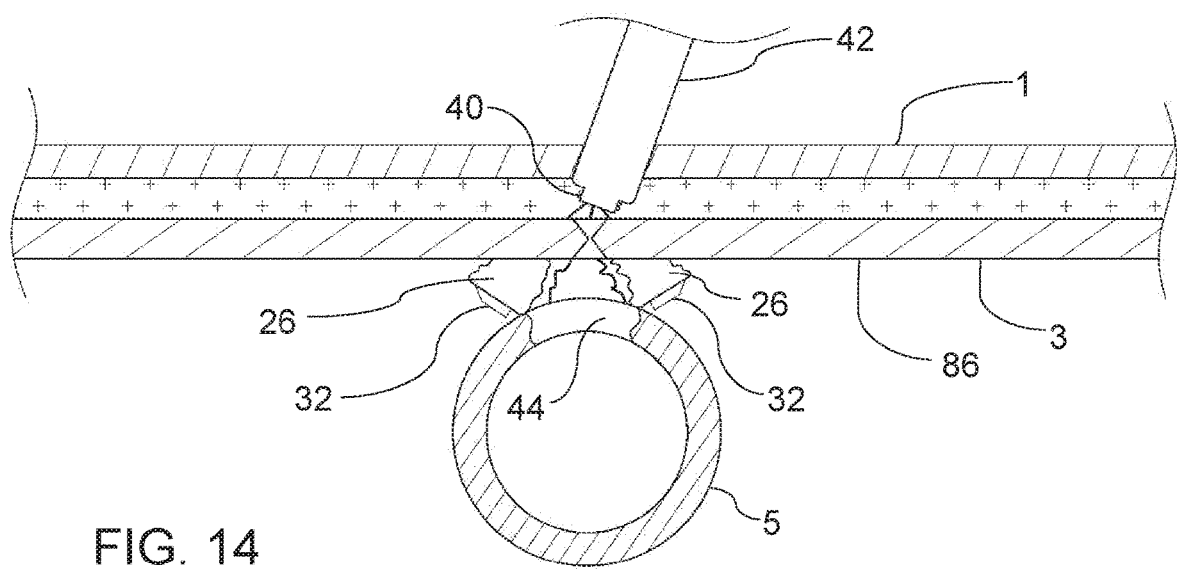
FIG. 14 shows the filaments of the vascular closure device in a tensioned state with the collapsible tubes in a compressed and radially expanded state prior to deployment of a lock ring over the filaments.

FIG. 12 depicts partially retracting the anchor 32 of each of the anchor deployers 28 by proximally retracting a filament 30 which is secured to the respective anchor 32. FIGS. 13 and 14 depict axially compressing the collapsible tube 26 of each of the plurality of anchor deployers 28 between the respective anchor 32 and lower surface 86 of the tissue layer 3 by applying tension to the filament 30 which is secured to the anchor 32 and which is disposed within an inner lumen of the collapsible tube 26. Tension is applied to the filament 30 until the collapsible tube 26 shortens in axial length and expands in an outward radial direction adjacent the access passage 38. Tension may be applied to the filaments 30 from the distal section 54 of the housing 36 by actuation of the filament tensioner 70 in order to reduce a distance between the anchors 32, thereby drawing the anchors 32 and adjacent tissue of the tissue layer 3 radially inward so as to reduce the size of the access passage 38 in the tissue layer 3.

In some cases, a filament grip which may be configured as a self-contracting lock ring 40 as shown in FIG. 15 may be deployed onto the filaments 30 in order to secure the filaments 30 relative to each other at the lock ring 40 after the size of the access passage 38 in the tissue layer 3 has been reduced. The self-contracting lock ring 40 may be deployed onto the filaments 30 by sliding the self-contracting lock ring 40 in an expanded state from the distal end 42 of the housing 36, then allowing the self-contracting lock ring 40 to contract to a relaxed state over the filaments 30.

In some cases collapsible tubes 26 formed from a thrombogenic material may be utilized, and upon deployment into a blood field which is below the tissue layer thrombus may form adjacent to the collapsible tubes 26 as shown in FIG. 15. Additionally, in some instances the collapsible tubes 26 may be configured with a proximal section 46 which has been configured to be mechanically stopped by a bottom surface 86 of the fascia tissue layer 3 adjacent the proximal section 46 as has been discussed previously. In this case the method which is depicted in FIGS. 10-15 may further include preferentially radially expanding and axially collapsing the proximal end 84 and/or proximal section 46 of the collapsible tubes 26 against the lower surface 86 of the fascia tissue layer 3 in an outward radial direction due to the slotted or otherwise weakened wall structure 76 of the collapsible tubes 26 at the proximal section 46 thereof while axially compressing the collapsible tubes 26 while proximally tensioning the filaments 30. Radially expanding and axially collapsing a proximal end 46 of collapsible tubes 26 may include in some cases splaying leafs of respective proximal ends 84 of collapsible tube embodiments 26 that include proximal slits 82 from the proximal ends 84 of the collapsible tubes 26 as shown in the collapsible tube embodiment of FIG. 9A.

The method which is depicted in FIGS. 10-15 may also include alternative methods for mechanically stopping the proximal sections 46 of the collapsible tubes 26 such as disposing a flared proximal end 84 of collapsible tube embodiments 26 against the lower surface 86 of the tissue layer 3 and spaced from the edge of the puncture hole 50 formed by the respective anchor deployers 28, and crumpling the proximal ends 84 of the collapsible tubes 26 which have a reduced wall thickness (as shown in the collapsible tube embodiment 26 of FIG. 9B) against the lower surface 86 of the tissue layer 3.

Figure 16:
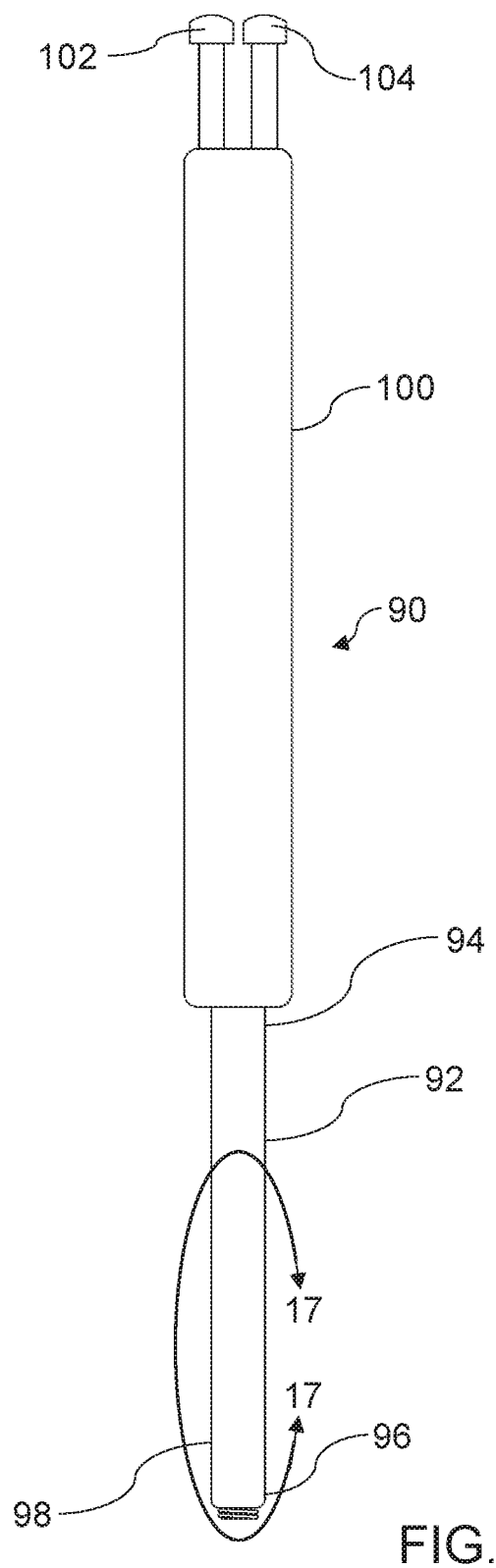
FIG. 16 illustrates an embodiment of a hemostasis device.
Figure 17:
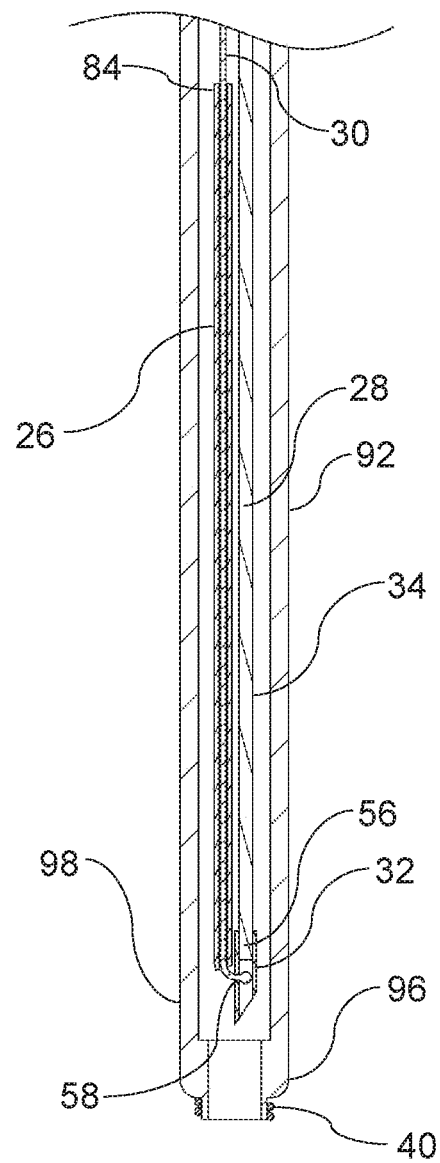
FIG. 17 is an enlarged view in partial section of a distal section of a housing of the hemostasis device embodiment of FIG. 16.

During some surgical procedures, it may be desirable to deploy a device that is suitable for reducing bleeding in targeted areas without also closing an access passage 38 at the same time. Such a hemostasis device may be intended to close "spots" of bleeding after a vascular closure procedure, such as bleeding from a puncture hole caused by the insertion of an anchor deployer or any other suitable location. FIGS. 16 and 17 show an embodiment of a hemostasis device 90 that includes a housing 92 having an elongate configuration with an axial length of the housing 92 may be greater than a transverse dimension of the housing 92. The housing 92 may also include a proximal end 94, a distal end 96, and a distal section 98.

The hemostasis device 90 may include a single anchor deployer 28 that may be suitably disposed within an interior volume of the housing 92 as shown in FIG. 17. The anchor deployer 28 may be configured to extend from the distal section 98 of the housing 92 and into target tissue during a hemostasis procedure. The anchor deployer 28 may include the deployment rod 34, the anchor 32, the filament 30, and the collapsible tube 26 that may be disposed over the filament 30. The collapsible tube 26 may include features, materials, and dimensions which are the same as or similar to those features, materials and dimensions of collapsible tube embodiments 26 discussed above. The deployment rod 34 may have an elongate resilient configuration, and may be slidably disposed relative to the housing 92 such that the distal end 56 of the deployment rod 34 may extend distally and radially from the distal section 98 of the housing 92 upon deployment of the anchor deployer 28.

The anchor 32 of the anchor deployer 28 may be removably secured to the distal end 56 of the deployment rod 34. The anchor 32 may be configured to penetrate tissue 3 in a distal direction and optionally prevent tissue penetration of the fascia tissue layer 3 in a proximal direction. The anchor 32 may optionally be configured to facilitate the deployment of the anchor deployer 28 distally into the target tissue 3 while allowing for the mechanical capture of the anchor 32 by surrounding tissue 3 upon retraction of the deployment rod 34 and proximal tensioning of the filament 30.

The anchor deployer 28 of the hemostasis device 90 may also include the filament 30 that may be slidably disposed within the housing 92 and which may include the distal end 58 that may be secured to the anchor 32. The anchor deployer 28 may also include the collapsible tube 26 that may be disposed over and secured to a distal section of the filament 30, the distal section 60 of the filament 30 being disposed such that it is proximal of and adjacent to the anchor 32. In some cases, the collapsible tube 26 may have an elongate configuration such that an axial length of the collapsible tube 26 may be greater than a transverse dimension of the collapsible tube 26. Additionally, the collapsible tube 26 may have a wall structure 76 that may be configured to buckle in an axial orientation upon axial compression of the collapsible tube 26.

In some instances, the housing 92 may include a guidewire lumen (not shown) which may extend the axial length of the housing 92 from the proximal end 94 to the distal end 96. The guide wire lumen may be configured to allow for the passage of a guidewire 8 through the housing 92. In some cases, a guidewire 8 may remain within a target vessel and within a vascular access channel created during the percutaneous cardiovascular procedure. The guidewire lumen disposed within the housing 92 of the hemostasis device 90 allows for the vascular closure device to be coupled to the guidewire 8 thereby allowing for the tracking of the hemostasis device 90 along the guidewire 8 within the vascular access passage 38 or access hole 44 the artery 5 if applicable.

The hemostasis device 90 may also include a handle 100 that may be secured to the proximal end 94 of the housing 92. The handle 100 may be utilized in order to grasp and manipulate the hemostasis device 90 during a vascular closure procedure, and may include features which control the insertion of the anchor deployer 28 (via distal extension of the rod pusher 102), proximal retraction of the deployment rod 34, proximal tensioning of the filament 30, and in some cases deployment of a lock ring 40. The handle 100 may include a Luer lock (not shown) which allows for access through the handle 100 to the guidewire lumen which may be disposed within the housing 92.

The rod pusher 102 may be operatively coupled to the deployment rod 34, in some cases the rod pusher 102 may be operatively coupled to a proximal end of the deployment rod 34. The rod pusher 102 may be configured such that it can slide within the handle 100 both distally and proximally, thereby allowing for the rod pusher 102 to be utilized in order to distally extend or proximally retract the deployment rod 34 during a vascular closure procedure. The handle 100 may also include a filament tensioner 104 which may be operatively coupled to the filament 30. The filament tensioner 104 may be configured such that it can slide proximally within the handle 100, thereby allowing for the filament tensioner 104 to be utilized in order to proximally tension the filament 30.

The hemostasis device 90 may also include a filament grip feature that may be configured as the lock ring 40 and that may function to mechanically capture the filament 30 after proximal tensioning. In some cases the lock ring 40 may be disposed on the distal end 96 of the housing 92 (see FIG. 17) adjacent the filament 30, and may be configured to compress and secure the filament 30 once deployed from an expanded state on the distal end 96 of the housing 92. For some embodiments the lock ring 40 may be configured as a self-retracting coil having a central lumen 41 which may be disposed about the filament 30. In some cases the lock ring 40 may be sized in order to allow free movement of the filament 30 when the self-retracting lock ring 40 is disposed in an expanded state. In turn the lock ring 40 may have an interior surface of the central lumen 41 that is configured to compress and be secured to the filament 30 when the lock ring 40 is disposed a retracted state.

As discussed above, the anchor 32 may optionally act to mechanically capture surrounding tissue after deployment of the anchor deployer 28 and upon proximal tensioning of the filament. In some cases the anchor 32 may be sized and configured to present a surface area adjacent to the connection between the filament 30 and the anchor 32 that is wider than an outer transverse dimension of the collapsible tube which may prevent the filament 30 and anchor 32 from being pulled through the inner lumen of the collapsible tube 26 upon tensioning of the filament 30 against the lower surface of the fascia tissue layer 3. In some instances the anchor 32 may be configured to rotate, pivot or expand after being deployed from the distal end 56 of the deployment rod 34. In some cases the anchor 32 may be formed from a hypo tube section which has an inclined sharpened end portion.

Figure 18:
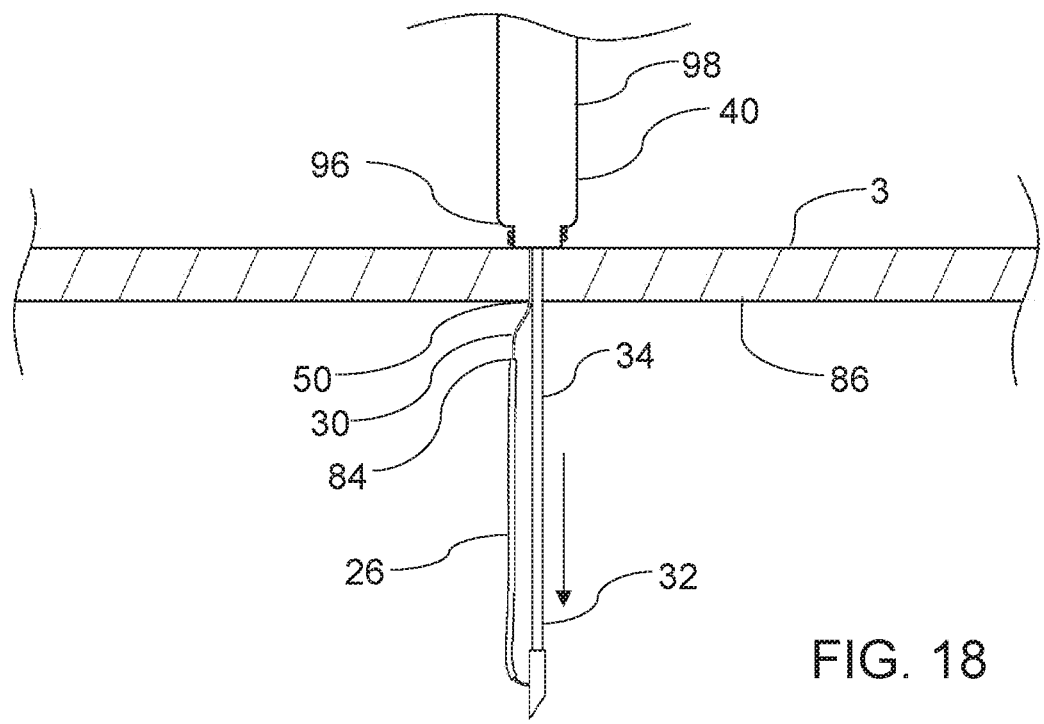
FIG. 18 shows an anchor deployer embodiment of the hemostasis device embodiment of FIG. 17 disposed through a fascia tissue layer.
Figure 19:
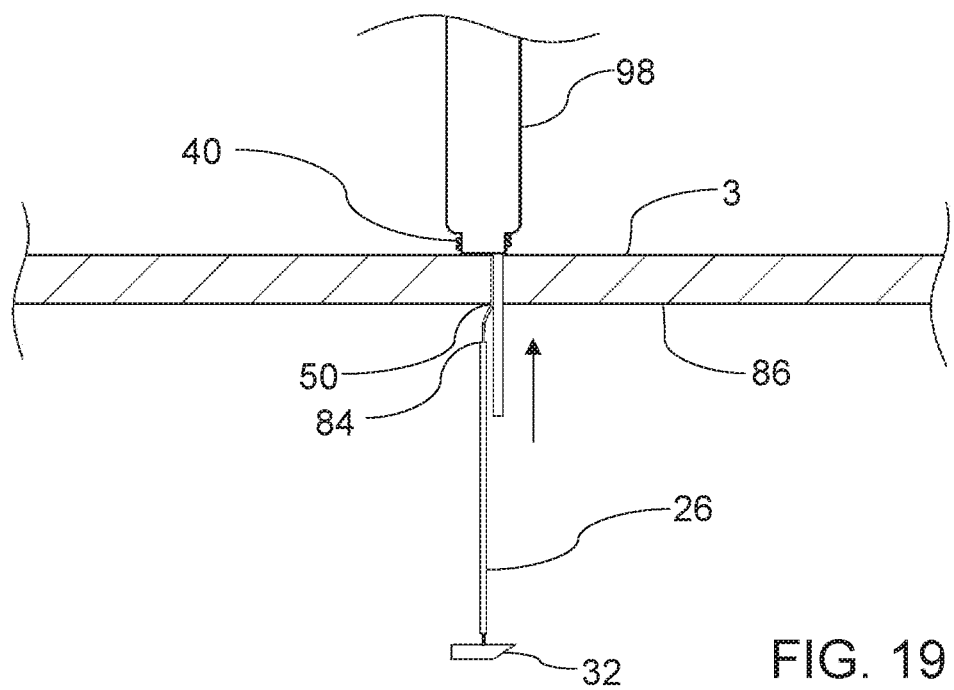
FIG. 19 shows the hemostasis device of FIG. 18 with a deployment rod thereof being proximally retracted.

FIGS. 18-21 depict a method for the deployment of the hemostasis device 90 in order to prevent or reduce blood leakage from a vascular closure site in a tissue layer 3. FIG. 18 depicts disposing a distal end 96 of a housing 92 of the hemostasis device 90 to a position adjacent the access passage 38 in the tissue layer 3, as well as the deploying of the anchor deployer 28 from the distal section 98 of the housing 92 in a distal direction from the housing 92 in the tissue layer 3. The anchor deployer 28 may be deployed distally by distally advancing the deployment rod 34 from the housing 92. The anchor deployer 28 of the hemostasis device 90 is shown to be penetrating the tissue layer 3 and extending through the tissue layer 3 until a proximal end 84 of the collapsible tube 26 of the anchor deployer 28 extends distally beyond a lower surface 86 of the tissue layer 3. FIG. 19 depicts proximally withdrawing the deployment rod 34 of the anchor deployer 28 from the anchor 32 and into the distal section 98 of the housing 92.

Figure 20:
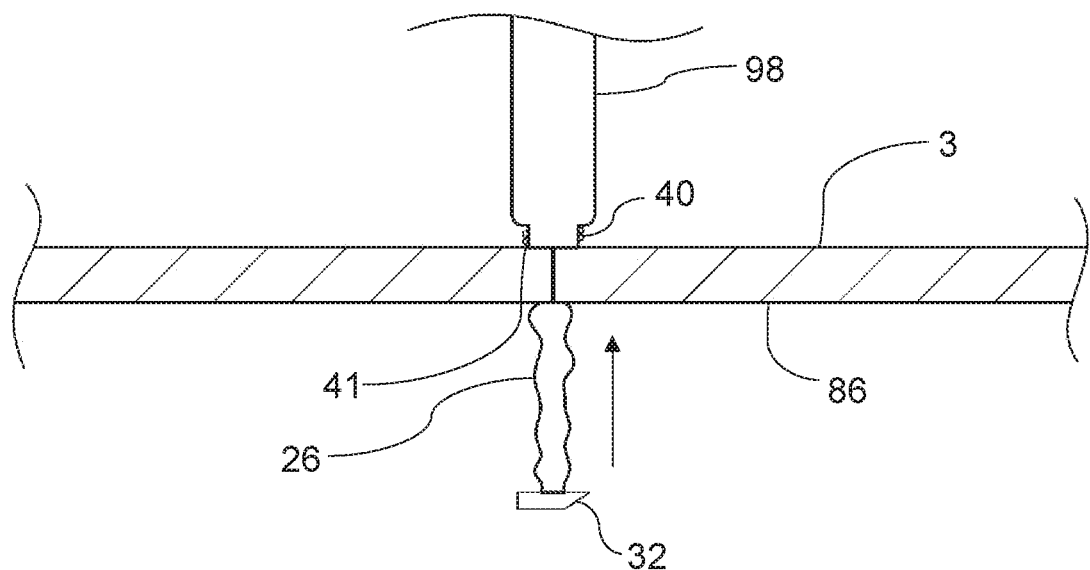
FIG. 20 shows proximal tension being applied to a filament of the hemostasis device embodiment of FIG. 19.

FIG. 19 depicts partially retracting the anchor 32 of the anchor deployer 28 by proximally retracting the filament 30 which may be secured to the anchor 32 with the filament tensioner 104. FIG. 20 depicts axially compressing the collapsible tube 26 of the anchor deployer 28 between the anchor 32 and lower surface 86 of the tissue layer 3 by applying tension to the filament 30 which may be secured to the anchor 32 and which may be disposed within an inner lumen of the collapsible tube 26. Tension is applied to the filament 30 until the collapsible tube 26 shortens in axial length and expands in an outward radial direction adjacent the puncture hole 50.

In some Instances, the lock ring 40 which may be configured as a self-contracting lock ring (see FIG. 17) may be deployed onto the filament 30 after tensioning in order to secure the filament 30 relative to the fascia tissue layer 3 to prevent distal movement of the filament 30 through the tissue layer 3. The self-contracting lock ring 40 may be deployed onto the filament 30 by sliding the self-contracting lock ring 40 in an expanded state from the distal end 96 of the housing 92, then allowing the self-contracting lock ring 40 to contract to a relaxed state over the filament 30.

Figure 21:
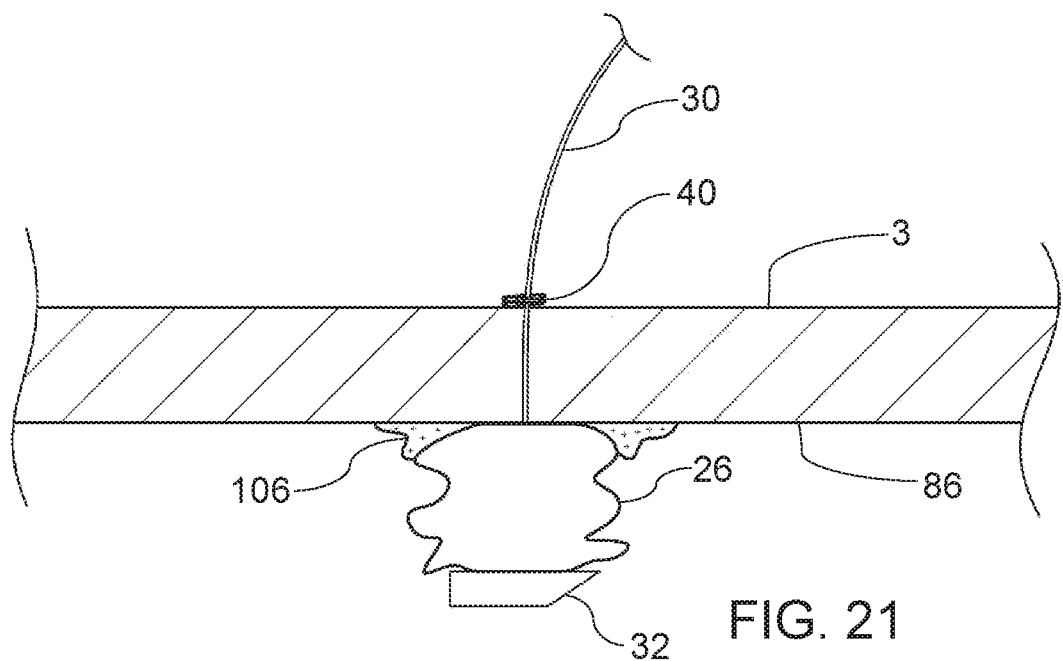
FIG. 21 shows a collapsible tube of the hemostasis device embodiment of FIG. 20 in an axially collapsed and radially expanded deployed state.

In some cases the collapsible tube 26 may be formed from a thrombogenic material, and upon deployment into a blood field which is below the tissue layer 3 thrombus may form adjacent to the collapsible tube 26 as shown in FIG. 21. Additionally, in some instances the collapsible tube 26 may be configured with a proximal section which has been configured to be mechanically stopped from passing back through the puncture hole 50 as has been discussed previously. In this case the method which is depicted in FIGS. 18-21 may further include radially expanding and axially collapsing the proximal end 84 of the collapsible tube 26 against the lower surface 86 of the tissue layer 3 in an outward radial direction while axially compressing the collapsible tube 26 while proximally tensioning the filament 30. Radially expanding and axially collapsing a proximal end 84 of collapsible tube 26 may include in some cases splaying leafs of a proximal end 84 of the collapsible tube 26 that include proximal slits 82 from the proximal end 84 of the collapsible tube 26.

The method which is depicted in FIGS. 18-21 may also include alternative methods for mechanically stopping the proximal section 46 of the collapsible tube 26 from passing through the puncture hole 50 in a proximal direction such as disposing a flared proximal end 84 of the collapsible tube 26 against the lower surface 86 of the tissue layer 3 and spaced from the puncture hole 50 formed by deployment of the anchor deployer 28, and crumpling the proximal end 84 of the collapsible tube 26 which has a reduced wall thickness against the lower surface 86 of the tissue layer 3.

Embodiments illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation and use of such terms and expressions do not exclude any equivalents of the features shown and described or portions thereof, and various modifications are possible. The term "a" or "an" can refer to one of or a plurality of the elements it modifies (e.g., "a reagent" can mean one or more reagents) unless it is contextually clear either one of the elements or more than one of the elements is described. Thus, it should be understood that although embodiments have been specifically disclosed by representative embodiments and optional features, modification and variation of the concepts herein disclosed may be resorted to by those skilled in the art, and such modifications and variations are considered within the scope of this disclosure.

With regard to the above detailed description, like reference numerals used therein refer to like elements that may have the same or similar dimensions, materials and configurations. While particular forms of embodiments have been illustrated and described, it will be apparent that various modifications can be made without departing from the spirit and scope of the embodiments of the invention. Accordingly, it is not intended that the invention be limited by the forgoing detailed description.

What is claimed is:

1. A vascular closure device, comprising:
   a housing including an elongate configuration with an axial length greater than a transverse dimension thereof, a proximal end, a distal end and a distal section;
   a plurality of anchor deployers configured to extend from the distal section of the housing, each anchor deployer comprising:
     a deployment rod which is slidably disposed relative to the housing and which includes an elongate resilient configuration and a distal end that extends distally and radially from the distal section of the housing,
     an anchor which is removably secured to the distal end of the deployment rod and which is configured to penetrate tissue in a distal direction,
     a filament which is slidably disposed within the housing and which includes a distal end which is secured to the anchor, and
     a collapsible tube disposed over a distal section of the filament proximal of and adjacent to the anchor, the collapsible tube including an elongate configuration having an axial length greater than a transverse dimension thereof, a wall structure that is configured to shorten in axial length and radially expand upon axial compression and a distal end which is fixedly secured to the filament with a remainder of the collapsible tube sized to slide freely in an axial direction over an outer surface of the filament; and
   wherein the filaments of the plurality of anchor deployers are slidably disposed within the housing adjacent each other at the distal section of the housing.

2. The vascular closure device of claim 1 wherein the housing further comprises a guidewire lumen extending an axial length thereof.

3. The vascular closure device of claim 1 further comprising a handle secured to the proximal end of the housing.

4. The vascular closure device of claim 1 further comprising a rod pusher operatively coupled to each of the deployment rods.

5. The vascular closure device of claim 1 further comprising a filament tensioner operatively coupled to the filament of each anchor deployer.

6. The vascular closure device of claim 1 wherein each of the collapsible tubes comprises a distal section which tapers distally to a reduced outer transverse dimension.

7. The vascular closure device of claim 1 wherein each of the collapsible tubes comprises a longitudinal slit in a middle section of a wall thereof.

8. The vascular closure device of claim 7 wherein each of the collapsible tubes comprises a plurality of longitudinal slits in a middle section in the wall thereof.

9. The vascular closure device of claim 1 wherein each of the collapsible tubes comprises a material selected from the group consisting of polyurethane, polyethylene terephthalate (PET), polyether ether ketone (PEEK), polytetrafluoroethylene (PTFE), acrylic, silicone, polypropylene, and polyester.

10. The vascular closure device of claim 1 wherein each of the collapsible tubes comprises a thrombogenic material.

11. The vascular closure device of claim 10 wherein the thrombogenic material comprises a material selected from the group consisting of collagen, fibrin, fibrinogen, gelatin, polylactic acid (PLA), polyglycolic acid (PGA), alginate and fibronectin.

12. The vascular closure device of claim 1 wherein each of the collapsible tubes comprises a hydrogel material that swells to a larger volume over time in an aqueous environment.

13. The vascular closure device of claim 12 wherein the hydrogel material comprises a material selected from the group consisting of fibrin, collagen, gelatin, hyaluronic acid, alginate, agarose, poly(ethylene glycol), poly(acrylic acid), poly(vinyl alcohol), polypeptides, and poly(vinyl pyrrolidone).

14. The vascular closure device of claim 1 wherein each of the collapsible tubes comprises a slit through the wall of the tube extending distally from the proximal end of the collapsible tube.

15. The vascular closure device of claim 14 wherein each of the collapsible tubes comprises a plurality of slits through the wall extending distally from the proximal end of the collapsible tube.

16. The vascular closure device of claim 15 wherein the plurality of slits through the wall extending distally from the proximal end of the collapsible tube comprise a length of about 1 mm to about 4 mm.

17. The vascular closure device of claim 1 wherein each of the collapsible tubes has a wall thickness that tapers to a reduced wall thickness from a position which is distal of the proximal end of the collapsible tube to a position at the proximal end of the collapsible tube.

18. The vascular closure device of claim 1 each of wherein the collapsible tubes flare proximally to a larger outer transverse dimension from a position which is distal of the proximal end of the collapsible tube to a position at the proximal end of the collapsible tube.

19. The vascular closure device of claim 1 wherein each of the collapsible tubes comprises an axial length of about 3 mm to about 15 mm.

20. The vascular closure device of claim 1 wherein each of the collapsible tubes comprises an outer transverse dimension of about 0.5 mm to about 2 mm.

21. The vascular closure device of claim 1 further comprising a filament grip that is disposed on the distal end of the housing adjacent the filaments and which is configured to compress and secure the filaments relative to each other once deployed from the distal end of the housing.

22. The vascular closure device of claim 21 wherein the filament grip comprises a lock ring disposed about the filaments which includes a self-retracting coil with a central lumen which is disposed about the filaments, which is sized to allow free movement of the filaments with the self-retracting coil in an expanded state and which has an interior surface of the central lumen that is configured to compress the filaments when in a retracted state.

23. The vascular closure device of claim 1 further comprising a lateral surface configured to extend radially from a distal extension of the housing while the lateral surface is disposed within a blood vessel to provide a reference point between axial relative positions of the wall of the blood vessel and the anchors prior to deployment of the anchors.

24. The vascular closure device of claim 23 wherein the anchors can be deployed a predetermined axial distance from the wall of the blood vessel as measured from the lateral surface which is disposed against the wall of the blood vessel.

* * * * *